US012668821B2

(12) United States Patent
Master et al.

(10) Patent No.: US 12,668,821 B2
(45) Date of Patent: Jun. 30, 2026

(54) ENZYMATIC PRODUCTION OF GLUCARIC ACID FROM GLUCURONIC ACID

(71) Applicant: THE GOVERNING COUNCIL OF THE UNIVERSITY OF TORONTO, Ontario (CA)

(72) Inventors: Emma R. Master, Toronto (CA); Thu V. Vuong, Toronto (CA)

(73) Assignee: THE GOVERNING COUNCIL OF THE UNIVERSITY OF TORONTO, Toronto (CA)

( * ) Notice: Subject to any disclaimer, the term of this patent is extended or adjusted under 35 U.S.C. 154(b) by 782 days.

(21) Appl. No.: 17/595,422

(22) PCT Filed: May 15, 2020

(86) PCT No.: PCT/CA2020/050658
§ 371 (c)(1),
(2) Date: Nov. 16, 2021

(87) PCT Pub. No.: WO2020/232536
PCT Pub. Date: Nov. 26, 2020

(65) Prior Publication Data
US 2022/0315957 A1    Oct. 6, 2022

Related U.S. Application Data

(60) Provisional application No. 62/849,377, filed on May 17, 2019.

(51) Int. Cl.
*C12P 7/58* (2006.01)
*C12N 9/04* (2006.01)

(52) U.S. Cl.
CPC .............. *C12P 7/58* (2013.01); *C12N 9/0006* (2013.01)

(58) Field of Classification Search
CPC ................................. C12P 7/58; C12N 9/0006
See application file for complete search history.

(56) References Cited

U.S. PATENT DOCUMENTS 9,227,904 B1    1/2016  Hong et al.
2014/0057332 A1    2/2014  Foumani et al.

OTHER PUBLICATIONS

International Preliminary Report on Patentability dated Nov. 16, 2021, prepared in International Application No. PCT/CA2020/050658.
Armstrong RD, et al. "How to synthesise high purity, crystalline D-glucaric acid selectively" European J Org Chem. 2017; 2017:6811-4.
Bertaud F. "Evaluation of acid methanolysis for analysis of wood hemicelluloses and pectins" Carbohydrate Polymers. 2002;48:319-24.

Bozell JJ, et al. "Technology development for the production of biobased products from biorefinery carbohydrates—the US Department of Energy's Top 10" revisited. Green Chemistry. 2010;12:539.
Chen N, et la. "Metabolic engineering of Saccharomyces cerevisiae for efficient production of glucaric acid at high titer" Microbial Cell Factories. 2018;17:67.
De Ruiter GA, et al. "Carbohydrate analysis of water-soluble uronic acid-containing polysaccharides with high-performance anion-exchange chromatography using methanolysis combined with TFA hydrolysis is superior to four other methods" Anal Biochem. 1992;207:176-85.
Foumani M, et al. "Altered substrate specificity of the gluco-oligosaccharide oxidase from *Acremonium strictum*" Biotechnol Bioeng. 2011;108:2261-9.
International Search Report prepared for PCT/CA2020/050658.
Irwin D, et al "Characterization and sequence of a Thermomonospora fusca xylanase" Appl Environ Microbiol. 1994;60:763-70.
Kim Jh, et al. "Purification and characterization of Thermobifida fusca xylanase 10B" Can J Microbiol. 2004;50:835-43.
Lee CC, et al. "Production of glucaric acid from hemicellulose substrate by rosettasome enzyme assemblies" Mol Biotechnol. 2016a;58:489-96.
Lee J, et al. "Pt catalysts for efficient aerobic oxidation of glucose to glucaric acid in water. Green Chemistry" 2016b;18:3815-22.
Lin S-F, et al., "Purification and characterization of a novel glucooligosaccharide oxidase from *Acremonium strictum* T1", Biochim Biophys Acta. 1991;1118:41-7.
Liu Y, Gong X, et al. "Production of glucaric acid from myo-inositol in engineered Pichia pastoris" Enzyme Microb Technol. 2016;91:8-16.
Löwendahl L, et al. "Formation of dicarboxylic acids from 4-O-methyl-D-glucuronic acid in alkaline solution in the presence and absence of oxygen" Carbohydrate Research. 1975;43:355-9.
MacCormick B, et al., "Chemo-enzymatic synthesis of clickable xylo-oligosaccharide monomers from hardwood 4-O-methylglucuronoxylan" Biomacromolecules. 2018;19:521-30.
Moon TS, et al. "Production of glucaric acid from a synthetic pathway in recombinant *Escherichia coli*" Appl Environ Microbiol. 2009;75:589-95.
Rorrer NA, et al,., "Renewable unsaturated polyesters from muconic acid" ACS Sustainable Chemistry & Engineering. 2016;4:6867-76.
Signal-Aldrich, "D-Saccharic acid potassium salt" Sigma-Aldrich product catalog. Jul. 16, 2007. ISSN0414-0229.

(Continued)

*Primary Examiner* — Louise W Humphrey
*Assistant Examiner* — Rachel Emily Martin
(74) *Attorney, Agent, or Firm* — Barnes & Thornburg LLP

(57) ABSTRACT

Described herein are processes and enzymes for the enzymatic production of glucaric acid from glucuronic acid, and more specifically the enzymatic production of substituted glucaric acid from substituted glucuronic acid. Advantageously, the process and enzymes described herein make preferential use substituted glucuronic acid obtained from natural sources, such as underutilized hemicellulose stream from wood and agricultural biorefineries, to produce substantially enantiomerically pure substituted D-glucaric acid.

17 Claims, 13 Drawing Sheets

Specification includes a Sequence Listing.

(56) References Cited

OTHER PUBLICATIONS

Solmi S, et al. "The oxidation of D-glucose to glucaric acid using Au/C catalysts" ChemCatChem. 2017:DOI:10.1002/cctc. 201700089.

Teleman A, et al. "Characterization of O-acetyl-(4-O-methylglucurono)xylan isolated from birch and beech" Carbohydr Res. 2002;337:373-7.

Vuong TV, et al. "Xylo- and cello-oligosaccharide oxidation by gluco-oligosaccharide oxidase from *Sarocladium strictum* and variants with reduced substrate inhibition" Biotechnol Biofuels. 2013;6:148.

Vuong TV, et al. "Fusion of a xylan-binding module to gluco-oligosaccharide oxidase increases activity and promotes stable immobilization" PLOS One. 2014;9:e95170.

Vuong TV, et al. "Direct comparison of gluco-oligosaccharide oxidase variants and glucose oxidase: substrate range and $H_2O_2$ stability" Sci Rep. 2016;6:37356.

Vuong TV, et al. "Enzymatic production of 4-O-methyl-D-glucaric acid from hardwood xylan" Biotechnol Biofuels (2020) 13:51.

Wang W, et al., "Biochemical and structural characterization of a five-domain GH115 α-glucuronidase from the marine bacterium Saccharophagus degradans 2-40T" J Biol Chem. 2016;291(27):14120-33.

Yan R, et al. "Action of a GH115 alpha-glucuronidase from Amphibacillus xylanus at alkaline condition promotes release of 4-O-methylglucopyranosyluronic acid from glucuronoxylan and arabinoglucuronoxylan" Enzyme Microb Technol. 2017;104:22-8.

Yazici EY, et al. "Factors affecting decomposition of hydrogen peroxide" Proceedings of the XIIth International Mineral Processing Symposium 2010. p. 609-16.

Lin, S.F., et al., Production of novel oligosaccharide oxidase by wheat bran solid-state fermentation. Biotechnol Adv, 1993. 11(3): p. 417-27.

Lin, S.-F., Y.-L. Hwang, and Y.-C. Tsai, Immobilization of glucooligosaccharide oxidase of *Acremonium strictum* for oligosaccharic acid production. Biotechnol Tech, 1996. 10(1): p. 63-68.

Fan, Z., G.B. Oguntimein, and P.J. Reilly, Characterization of kinetics and thermostability of *Acremonium strictum* glucooligosaccharide oxidase. Biotechnol Bioeng, 1999. 68(2): p. 231-7.

Huang, C.H., et al., Crystal structure of glucooligosaccharide oxidase from *Acremonium strictum*: a novel flavinylation of 6-S-cysteinyl, 8alpha-N1-histidyl FAD. J Biol Chem, 2005. 280(46): p. 38831-8.

Lee, M.H., et al., Structural characterization of glucooligosaccharide oxidase from *Acremonium strictum*. Appl Environ Microbiol, 2005. 71(12): p. 8881-7.

Huang, C.H., et al., Functional roles of the 6-S-cysteinyl, 8alpha-N1-histidyl FAD in glucooligosaccharide oxidase from *Acremonium strictum*. J Biol Chem, 2008. 283(45): p. 30990-6.

Nakano, H., et al., Biocatalytic Production of Lactobionic Acid, in Biocatalysis and Biomolecular Engineering. 2010, John Wiley & Sons, Inc. p. 391-404.

Foumani, M., et al., Enhanced polysaccharide binding and activity on linear beta-glucans through addition of carbohydrate-binding modules to either terminus of a gluco-oligosaccharide oxidase. PLoS One, 2015. 10(5): p. e0125398.

Fig. 1

4-O-methylglucuronoxylan

AxyAgu115A    GOOX    FAD

4-O-methyl-glucaric acid

SEQUENCE LISTING

```
<160> NUMBER OF SEQ ID NOS: 5

<210> SEQ ID NO 1
<211> LENGTH: 474
<212> TYPE: PRT
<213> ORGANISM: Sarocladium strictum
<220> FEATURE:
<221> NAME/KEY: MISC_FEATURE
<222> LOCATION: (1)..(206)
<223> OTHER INFORMATION: FAD-binding domain
<220> FEATURE:
<221> NAME/KEY: MISC_FEATURE
<222> LOCATION: (207)..(474)
<223> OTHER INFORMATION: substrate-binding domain

<400> SEQUENCE: 1

Asn Ser Ile Asn Ala Cys Leu Ala Ala Ala Asp Val Glu Phe His Glu
```

-continued

```
1               5                    10                   15

Glu Asp Ser Glu Gly Trp Glu Met Asp Gly Thr Ala Phe Asn Leu Arg
            20                25                30

Val Asp Tyr Asp Pro Val Ala Ile Ala Ile Pro Arg Ser Thr Glu Asp
            35                40                45

Ile Ala Ala Ala Val Gln Cys Gly Leu Asp Ala Gly Val Gln Ile Ser
    50                55                60

Ala Lys Gly Gly Gly His Ser Tyr Gly Ser Tyr Gly Phe Gly Gly Glu
65                  70                75                  80

Asp Gly His Leu Met Leu Glu Leu Asp Arg Met Tyr Arg Val Ser Val
                85                90                95

Asp Asp Asp Asn Val Ala Thr Ile Gln Gly Gly Ala Arg Leu Gly Tyr
            100               105               110

Thr Ala Leu Glu Leu Leu Asp Gln Gly Asn Arg Ala Leu Thr His Gly
            115               120               125

Thr Cys Pro Ala Val Gly Ile Gly Gly His Val Leu Gly Gly Gly Tyr
    130               135               140

Gly Phe Ala Thr His Thr His Gly Leu Thr Leu Asp Trp Leu Val Gly
145                 150               155               160

Ala Thr Val Val Leu Ala Asp Ala Ser Ile Val His Val Ser Lys Thr
                165               170               175

Glu Asn Ala Asp Leu Phe Trp Ala Leu Arg Gly Gly Gly Gly Gly Phe
            180               185               190

Ala Ile Val Ser Glu Phe Glu Phe Asn Thr Phe Glu Ala Pro Glu Ile
            195               200               205

Ile Thr Thr Tyr Gln Val Thr Thr Thr Trp Asn Arg Lys Gln His Val
    210               215               220

Ala Gly Leu Lys Ala Leu Gln Asp Trp Ala Glu Asn Thr Met Pro Arg
225                 230               235               240

Glu Leu Ser Met Arg Leu Glu Ile Asn Ala Asn Ala Leu Asn Trp Glu
                245               250               255

Gly Asn Tyr Phe Gly Asn Ala Lys Asp Leu Lys Lys Val Leu Gln Pro
            260               265               270

Ile Met Lys Lys Ala Gly Gly Lys Ser Thr Ile Ser Lys Leu Val Glu
    275               280               285

Thr Asp Trp Tyr Gly Gln Ile Asn Thr Tyr Leu Tyr Gly Ala Asp Leu
    290               295               300

Asn Ile Thr Tyr Asn Tyr Asp Val His Glu Tyr Phe Tyr Ala Asn Ser
305               310               315               320

Leu Thr Ala Pro Arg Leu Ser Asp Glu Ala Ile Ser Ala Phe Val Asp
            325               330               335

Tyr Lys Phe Asp Asn Ser Ser Val Arg Pro Gly Arg Gly Trp Trp Ile
            340               345               350

Gln Trp Asp Phe His Gly Gly Lys Asn Ser Ala Leu Ala Ser His Ser
            355               360               365

Asn Asp Glu Thr Ala Tyr Ala His Arg Asp Gln Leu Trp Leu Trp Gln
    370               375               380

Phe Tyr Asp Asn Ile Tyr Asp Tyr Glu Asn Asn Thr Ser Pro Tyr Pro
385               390               395               400

Glu Ser Gly Phe Glu Phe Met Gln Gly Phe Val Ala Thr Ile Glu Asp
            405               410               415

Thr Leu Pro Glu Asp Arg Lys Gly Lys Tyr Phe Asn Tyr Ala Asp Thr
            420               425               430
```

```
Thr Leu Asp Lys Glu Glu Ala Gln Lys Leu Tyr Trp Arg Gly Asn Leu
        435                 440                 445

Glu Lys Leu Gln Ala Ile Lys Ala Lys Tyr Asp Pro Glu Asp Val Phe
    450                 455                 460

Gly Asn Val Val Ser Val Glu Pro Ile Ala
465                 470
```

```
<210> SEQ ID NO 2
<211> LENGTH: 206
<212> TYPE: PRT
<213> ORGANISM: Sarocladium strictum
<220> FEATURE:
<221> NAME/KEY: MISC_FEATURE
<222> LOCATION: (1)..(206)
<223> OTHER INFORMATION: FAD-binding domain of SEQ ID NO: 1

<400> SEQUENCE: 2

Asn Ser Ile Asn Ala Cys Leu Ala Ala Ala Asp Val Glu Phe His Glu
1               5                   10                  15

Glu Asp Ser Glu Gly Trp Glu Met Asp Gly Thr Ala Phe Asn Leu Arg
            20                  25                  30

Val Asp Tyr Asp Pro Val Ala Ile Ala Ile Pro Arg Ser Thr Glu Asp
        35                  40                  45

Ile Ala Ala Ala Val Gln Cys Gly Leu Asp Ala Gly Val Gln Ile Ser
    50                  55                  60

Ala Lys Gly Gly Gly His Ser Tyr Gly Ser Tyr Gly Phe Gly Gly Glu
65                  70                  75                  80

Asp Gly His Leu Met Leu Glu Leu Asp Arg Met Tyr Arg Val Ser Val
            85                  90                  95

Asp Asp Asp Asn Val Ala Thr Ile Gln Gly Gly Ala Arg Leu Gly Tyr
            100                 105                 110

Thr Ala Leu Glu Leu Leu Asp Gln Gly Asn Arg Ala Leu Thr His Gly
        115                 120                 125

Thr Cys Pro Ala Val Gly Ile Gly Gly His Val Leu Gly Gly Gly Tyr
        130                 135                 140

Gly Phe Ala Thr His Thr His Gly Leu Thr Leu Asp Trp Leu Val Gly
145                 150                 155                 160

Ala Thr Val Val Leu Ala Asp Ala Ser Ile Val His Val Ser Lys Thr
            165                 170                 175

Glu Asn Ala Asp Leu Phe Trp Ala Leu Arg Gly Gly Gly Gly Gly Phe
            180                 185                 190

Ala Ile Val Ser Glu Phe Glu Phe Asn Thr Phe Glu Ala Pro
        195                 200                 205
```

```
<210> SEQ ID NO 3
<211> LENGTH: 268
<212> TYPE: PRT
<213> ORGANISM: Sarocladium strictum
<220> FEATURE:
<221> NAME/KEY: MISC_FEATURE
<222> LOCATION: (1)..(268)
<223> OTHER INFORMATION: substrate-binding domain of SEQ ID NO: 1

<400> SEQUENCE: 3

Glu Ile Ile Thr Thr Tyr Gln Val Thr Thr Thr Trp Asn Arg Lys Gln
1               5                   10                  15

His Val Ala Gly Leu Lys Ala Leu Gln Asp Trp Ala Glu Asn Thr Met
            20                  25                  30
```

-continued

```
Pro Arg Glu Leu Ser Met Arg Leu Glu Ile Asn Ala Asn Ala Leu Asn
        35                  40                  45

Trp Glu Gly Asn Tyr Phe Gly Asn Ala Lys Asp Leu Lys Lys Val Leu
    50                  55                  60

Gln Pro Ile Met Lys Lys Ala Gly Gly Lys Ser Thr Ile Ser Lys Leu
65                  70                  75                  80

Val Glu Thr Asp Trp Tyr Gly Gln Ile Asn Thr Tyr Leu Tyr Gly Ala
                85                  90                  95

Asp Leu Asn Ile Thr Tyr Asn Tyr Asp Val His Glu Tyr Phe Tyr Ala
                100                 105                 110

Asn Ser Leu Thr Ala Pro Arg Leu Ser Asp Glu Ala Ile Ser Ala Phe
                115                 120                 125

Val Asp Tyr Lys Phe Asp Asn Ser Ser Val Arg Pro Gly Arg Gly Trp
    130                 135                 140

Trp Ile Gln Trp Asp Phe His Gly Gly Lys Asn Ser Ala Leu Ala Ser
145                 150                 155                 160

His Ser Asn Asp Glu Thr Ala Tyr Ala His Arg Asp Gln Leu Trp Leu
                165                 170                 175

Trp Gln Phe Tyr Asp Asn Ile Tyr Asp Tyr Glu Asn Asn Thr Ser Pro
                180                 185                 190

Tyr Pro Glu Ser Gly Phe Glu Phe Met Gln Gly Phe Val Ala Thr Ile
                195                 200                 205

Glu Asp Thr Leu Pro Glu Asp Arg Lys Gly Lys Tyr Phe Asn Tyr Ala
    210                 215                 220

Asp Thr Thr Leu Asp Lys Glu Glu Ala Gln Lys Leu Tyr Trp Arg Gly
225                 230                 235                 240

Asn Leu Glu Lys Leu Gln Ala Ile Lys Ala Lys Tyr Asp Pro Glu Asp
                245                 250                 255

Val Phe Gly Asn Val Val Ser Val Glu Pro Ile Ala
                260                 265
```

```
<210> SEQ ID NO 4
<211> LENGTH: 966
<212> TYPE: PRT
<213> ORGANISM: Amphibacillus xylanus

<400> SEQUENCE: 4
```

```
Met Asp Phe Thr Leu Asn Gln Glu Met Leu Met Thr Asp Thr Lys Ser
1                   5                   10                  15

Gly Ala Leu Phe Tyr Gln Glu Glu Glu Ala Leu Ser Gly Val Arg Lys
                20                  25                  30

Ile Ala Asn Lys Val Met His Asp Val Glu Leu Val Phe Gly Tyr Gln
                35                  40                  45

Pro Glu Ala Thr Lys Asp Arg Asp Met Leu Ser Arg His Ala Val Leu
    50                  55                  60

Tyr Gly Thr Val Gly His Ser Pro Leu Leu Asp Glu Leu Asn Lys Lys
65                  70                  75                  80

Glu Leu Ile Asp Leu Thr Glu Ile Ala Gly Lys Arg Glu Val Phe Leu
                85                  90                  95

Phe Gln Val Val Asp Gln Pro Ile Gln Gly Val Glu Lys Ala Leu Val
                100                 105                 110

Ile Ala Gly Ser Asp Lys Arg Gly Thr Ile Tyr Gly Leu Phe His Leu
                115                 120                 125

Ser Glu Lys Leu Gly Val Ser Pro Leu Val Asp Trp Ser Gly Val Leu
    130                 135                 140
```

-continued

```
Pro Ala Arg Lys Glu Ser Phe Ser Leu Lys Gly Asp Tyr Lys Tyr Val
145                 150                 155                 160

Ser Lys Glu Pro Ser Val Lys Tyr Arg Gly Phe Phe Ile Asn Asp Glu
                165                 170                 175

Trp Pro Ala Phe Gly Asn Trp Ser Ala Lys Asn Phe Gly Gly Phe Asn
                180                 185                 190

Ala Glu Met Tyr Asp His Val Phe Glu Leu Leu Leu Arg Leu Lys Gly
            195                 200                 205

Asn Tyr Leu Trp Pro Ala Met Trp Ser Ala Arg Phe Asn Asp Asp Gly
        210                 215                 220

Pro Gly Leu Ala Asn Val Glu Leu Ala Asp Glu Tyr Gly Val Ile Met
225                 230                 235                 240

Gly Ala Ser His His Glu Pro Cys Leu Arg Tyr Gly Glu Glu Tyr Lys
                245                 250                 255

Tyr Leu Arg Gly Pro Asp Ser Ile Tyr Gly Asp Ala Trp Asn Phe Ile
                260                 265                 270

Thr Asn Arg Glu Gly Ile Thr Lys Phe Trp Glu Asp Gly Leu Lys Arg
            275                 280                 285

Thr Gly His Phe Glu Asn Ile Ile Thr Ile Gly Met Arg Gly Glu Ala
        290                 295                 300

Asp Thr Lys Ile Met Gly Glu Asp Ala Thr Leu Glu Asp Asn Ile Asn
305                 310                 315                 320

Leu Leu Arg Asp Val Ile Gln Thr Gln Asn Lys Leu Ile Lys Glu His
                325                 330                 335

Val Asn Pro Asn Leu Lys Glu Val Pro Arg Met Leu Ala Leu Tyr Lys
                340                 345                 350

Glu Val Glu Pro Phe Phe Tyr Gly Asp Glu Asn Thr Pro Gly Leu Ile
            355                 360                 365

Asn Ser Glu Glu Leu Glu Asp Val Ile Leu Met Leu Cys Asp Asp Asn
        370                 375                 380

His Gly Asn Leu Arg Thr Leu Pro Thr Glu Asp Met Arg Lys His Ser
385                 390                 395                 400

Gly Gly Tyr Gly Met Tyr Tyr His Phe Asp Tyr His Gly Gly Pro Val
                405                 410                 415

Ser Tyr Glu Trp Ile Asn Ser Ser Tyr Leu Pro Lys Ile Trp Glu Gln
                420                 425                 430

Met Thr Met Ala Tyr Asp Phe Gly Val Arg Asp Leu Trp Ile Val Asn
            435                 440                 445

Val Gly Asp Ile Ala Thr Gln Glu Leu Pro Leu Ser Phe Phe Leu Asp
        450                 455                 460

Leu Ala Tyr Asp Phe Asp Lys Trp Gly Thr Asn Ala Ile Asn Lys Thr
465                 470                 475                 480

Asp Asp Tyr Thr Lys Gln Trp Ile Glu Gln Gln Phe Ala Gly Val Phe
                485                 490                 495

Asn Leu Glu Gln Lys Asp Lys Val Phe Glu Leu Leu Asn Gly Tyr Thr
                500                 505                 510

Lys Ile Ala His Asn Arg Arg Pro Glu Ala Met Asn Val Asp Val Tyr
            515                 520                 525

His Pro Val Asn Tyr His Glu Thr Asp Gln Leu Leu Asp Arg Ile Asp
        530                 535                 540

His Leu Leu Gly Leu Ala Glu Glu Leu Tyr Gln Glu Val Asp Gln Gln
545                 550                 555                 560
```

-continued

His Phe Thr Ala Tyr Phe Ala Leu Val Tyr Tyr Pro Thr Val Gly Asn
            565             570             575

Leu Asn Leu Gln Lys Met Trp Leu Leu Asn Gly Lys Asn Lys Tyr Ala
            580             585             590

Ala Gln Leu Asn Leu Ile Glu Ala Asn Lys Leu Ala Glu Gln Val Lys
            595             600             605

Ala Cys Leu Lys Arg Asp Gln Glu Ile Val Asp Glu Tyr His Thr Ile
        610             615             620

Ala Asp Gly Lys Phe Tyr Gly Met Gly Leu Ser Glu His Ile Gly Phe
625             630             635             640

Val His Trp Asn Glu Asp Glu Asn Lys Asn Pro Val Leu Ser Tyr Val
            645             650             655

Leu Pro Val Asn Lys Pro Arg Leu Leu Val Ser Ile Asp Gly Thr Glu
            660             665             670

Leu Arg Ser Glu Gly Ser Pro Trp His Val Asn Thr Leu Pro Leu Val
            675             680             685

Asp Phe Leu Glu Pro Asp Val Asn Gln Ala Ser Phe Thr Ile Ser Ser
        690             695             700

Val Ser Glu Lys Lys Ala Glu Tyr His Ile Ser Thr Asp Gln Asp Trp
705             710             715             720

Leu Ser Cys Ser Ala Ala Asn Gly Val Leu Asp Gly Lys Asn Lys Leu
            725             730             735

Ser Glu Thr Ile His Val Phe Val Asp Arg Asp Gly Leu Ala Asp Gln
            740             745             750

Ala Glu Gly Arg Ile Thr Val Lys Thr Pro Val Gly Lys Val Thr Ile
            755             760             765

Val Val Pro Val Val Asn Asn Asp Phe Thr Asn Tyr Pro Asp Met Thr
        770             775             780

Phe Val Asp Thr Lys Gly Tyr Ile Ser Ile Glu Ala Glu His Phe Ala
785             790             795             800

Thr Gln Lys Ala Thr Glu Asn Leu Asp Gly Thr Leu Asn Arg Phe Glu
            805             810             815

Val Leu Asp Gly Tyr Gly Lys Thr Leu Ser Ala Ile Lys Ala Phe Pro
            820             825             830

Thr Asp Thr His Tyr Gln Val Gly Lys Asp Ala Pro Phe Val Glu Tyr
        835             840             845

His Phe Val Thr Gln Glu Ala Gly Val Tyr Glu Leu Glu Phe Tyr Leu
        850             855             860

Gln Pro Ser Asn Pro Val Thr Arg Glu Gly Thr Met Tyr Ala Gly Ile
865             870             875             880

Gln Val Asn Glu Asn Asp Val Asp Val Ile Asn Val Leu Pro Asp Gly
            885             890             895

Tyr His Val Asp Gly Pro His Trp Gly Ile Asp Val Ile Asn Asn Ile
            900             905             910

Arg Thr Thr Lys Thr Lys Ile Thr Cys Glu Gln Gly Leu Asn Lys Leu
            915             920             925

Arg Ile Tyr Ala Val Ser Pro Gly Phe Ala Leu Glu Lys Ile Val Ile
        930             935             940

Tyr Pro Asp Gly Lys Lys Leu Ala Asn Ser Tyr Leu Gly Pro Asn Glu
945             950             955             960

Thr Tyr Tyr Val Gly Arg
            965

-continued

```
<210> SEQ ID NO 5
<211> LENGTH: 943
<212> TYPE: PRT
<213> ORGANISM: Saccharophagus degradans 2-40

<400> SEQUENCE: 5

Val Leu Ala Leu Gly Asp Ala Gly Tyr Ile Ser Phe Lys Ala Asn Gly
1               5                   10                  15

Gly Val Arg Leu Ala Asp Glu Glu His Leu Ala Ser Leu Leu Val Asp
            20                  25                  30

Thr Asn Asp Tyr Lys Gly Leu Gln Arg Ala Ala Ala Asp Leu Gln Thr
        35                  40                  45

Asp Met Gln Arg Val Thr Gly Lys Leu Pro Thr Leu His Ser Gln Leu
    50                  55                  60

Lys Asp Ala Gly Arg His Ala Val Ile Ile Gly Ser Val Gly Arg Ser
65                  70                  75                  80

Gly Leu Ile Gln Leu Leu Val Glu Gln Asn Lys Leu Asn Val Ala Asp
            85                  90                  95

Ile Glu Gly Gln Trp Glu Ala Tyr Lys Leu Val Val Val Asp Lys Pro
            100                 105                 110

Phe Pro Asn Ile Glu Lys Ala Leu Val Ile Ala Gly Ser Asp Met Arg
        115                 120                 125

Gly Ala Ile Phe Gly Val Tyr Asp Leu Ser Gln Gln Ile Gly Val Ser
    130                 135                 140

Pro Trp Tyr Trp Trp Ala Asp Val Pro Val Gln Pro Gln Ser Lys Leu
145                 150                 155                 160

Tyr Val Arg Gly Asp Thr His Ile Val Glu Gln Pro Lys Val Gln Tyr
            165                 170                 175

Arg Gly Ile Phe Leu Asn Asp Glu Ala Pro Ala Leu Thr Asn Trp Val
            180                 185                 190

His Ala Asn Tyr Gly Asn Tyr Asn Ser Gln Phe Tyr Thr Gln Val Phe
        195                 200                 205

Glu Leu Leu Leu Arg Leu Lys Ala Asn Phe Leu Trp Pro Ala Met Trp
    210                 215                 220

Asn Asn Ser Phe Ser Val Asp Asp Pro Leu Asn Pro Val Leu Ala Asn
225                 230                 235                 240

Glu Tyr Gly Ile Val Met Ser Thr Ser His His Glu Pro Met Met Arg
            245                 250                 255

Ala His Lys Glu Trp His Gly Met Gly Arg Trp Asp Phe Thr Thr Asn
            260                 265                 270

Ala Asp Ala Leu Lys Gln Phe Trp Arg Glu Gly Val Glu Arg Asn Ser
        275                 280                 285

Pro Tyr Glu Asn Ile Ile Thr Met Ala Met Arg Gly Asp Gly Asp Glu
    290                 295                 300

Ala Met Ser Glu Asp Ala Asn Val Glu Leu Leu Glu Gln Ile Val Glu
305                 310                 315                 320

Ala Gln Arg Asn Ile Ile Ala Glu Val Phe Glu Pro Lys Gly Lys Gln
            325                 330                 335

Val Thr Glu Val Pro Gln Val Trp Cys Leu Tyr Lys Glu Val Gln Asp
            340                 345                 350

Tyr Tyr Glu Lys Gly Met Arg Val Pro Asp Asp Ile Thr Leu Leu Trp
        355                 360                 365

Ala Asp Asp Asn Trp Gly Asn Ile Arg Arg Leu Pro Thr Ala Glu Glu
    370                 375                 380
```

-continued

```
Arg Lys Arg Ser Gly Gly Ala Gly Val Tyr Tyr His Phe Asp Tyr Val
385             390             395             400

Gly Gly Pro Arg Ser Tyr Arg Trp Ile Asn Thr Thr Pro Leu Ala Lys
            405             410             415

Ile Trp Glu Gln Met His Leu Ala Tyr Lys Tyr Glu Ala Asn Lys Ile
            420             425             430

Trp Ile Val Asn Val Gly Asp Leu Lys Pro Met Glu Ala Pro Ile Glu
            435             440             445

Tyr Phe Leu Glu Met Ala Trp Asn Pro Glu Gln Trp Pro Lys Glu Arg
        450             455             460

Ile Thr Gln Phe Ala Glu Leu Trp Ala Glu Arg Glu Phe Gly Pro Thr
465             470             475             480

Tyr Ala Lys Glu Ile Ala Gln Leu Val Gln Asp Tyr Thr Gln His Asn
            485             490             495

Gly Arg Arg Lys Pro Glu Leu Gln Glu Ala Lys Thr Tyr Ser Leu Leu
            500             505             510

Asn Tyr Asp Glu Ala Ala Arg Ile Glu Gln Gln Leu Thr Asp Met Glu
        515             520             525

Ser Arg Ala Glu Thr Leu Phe Asn Lys Ile Pro Ala Asn Gln Arg Asp
        530             535             540

Ala Tyr Tyr Gln Leu Val Met His Pro Val Leu Ala Ser Ala Thr Val
545             550             555             560

Thr Lys Met Tyr Ile Ala Gln Ala Arg Asn Arg Leu Tyr Ala Lys Gln
            565             570             575

Gly Arg Pro Ile Ala Asn Ser Tyr Gly Gln Gln Val Lys Glu Leu Phe
            580             585             590

Glu Lys Asp Ala Ala Leu Thr Lys Arg Tyr His Ser Ile Asn Asn Gly
        595             600             605

Lys Trp Asn His Phe Met Ser Gln Pro His Ile Gly Tyr Thr His Trp
        610             615             620

Asn Asn Pro Glu Asp Asn Ile Met Pro Val Val Ser Val Val Ser Lys
625             630             635             640

Gly Asn Asn Ala Asp Met Gly Val Ala Val Glu Gly Met Glu Pro Ala
            645             650             655

Trp Pro Thr Gln Asp Val Ala Phe Ala Leu Pro Thr Phe Thr Pro Tyr
            660             665             670

Gly Lys Gln Thr Lys Ile Leu Thr Val Phe Asn Lys Gly Val Lys Pro
            675             680             685

Leu Lys Phe Ser Val Ser Ser Gly Ala Ala Trp Leu Lys Val Ser Ala
        690             695             700

Ser Ser Gly Glu Ile Thr His Gln Glu Met Gln Ile Gln Val Ser Ile
705             710             715             720

Asp Trp Ala Lys Leu Pro Leu Gly Ile His Glu Ser Asn Val Thr Ile
            725             730             735

Lys Gly Pro Ser Trp Val Ala Ala Asn Ile Lys Val Thr Ala Asn Lys
            740             745             750

Pro Ala Lys Val Ile Pro Leu Lys Lys Leu Thr Gly Phe Val Glu Ala
            755             760             765

Asp Gly Tyr Ile Ser Phe Asp Ala Ala Ala Thr Thr His Ser Lys Ala
        770             775             780

Val Asp Gly Phe Glu Trp Gln Glu Ile Pro Ala His Gly Arg Thr His
785             790             795             800

Ser Ser Met Ser Val Tyr Pro Ile Arg Asp Ala Ser Phe Ala Ala Pro
```

-continued

```
                    805                     810                     815

Ala Asn Ala Ser Ala Asn Thr Ala Pro Gln Met His Tyr Ser Ile Thr
            820                     825                     830

Leu Leu Thr Ala Gly Glu Val Thr Val Glu Gly Leu Phe Ala Pro Thr
            835                     840                     845

Trp Pro Ile His Pro Glu Arg Gly Leu Arg Tyr Ala Ile Ala Phe Asp
        850                     855                     860

Asp Gln Pro Pro Gln Ile Val Asp Val Leu Ala Gly Asn Ser His Lys
865                     870                     875                     880

Val Trp Gln Glu Ser Val Arg Thr Gly Val Arg Arg Ala Ser Ser Lys
            885                     890                     895

His Thr Leu Thr Ala Gly Thr His Thr Met Lys Val Trp Ala Ile Asp
            900                     905                     910

Pro Ala Val Thr Val Gln Lys Trp Ile Ile Asp Thr Gly Glu Leu Lys
            915                     920                     925

Pro Ser Tyr Leu Gly Pro Thr Pro Ser Pro Arg Gly Gly Lys His
        930                     935                     940
```

ENZYMATIC PRODUCTION OF GLUCARIC ACID FROM GLUCURONIC ACID

This application is a National Stage application of International Application No. PCT/CA2020/050658, filed May 15, 2020, which claims the benefit of U.S. Provisional Application No. 62/849,377, filed May 17, 2019, each of which are hereby incorporated by reference in their entireties.

The present description relates to the enzymatic production of substituted or unsubstituted glucaric acid from substituted or unsubstituted glucuronic acid. More specifically, the present description relates to the production of D-glucaric acid or 4-O-methyl D-glucaric acid from D-glucuronic acid or 4-O-methyl D-glucuronic acid, which can be obtained from natural sources, such as wood hemicelluloses, corn fibre, and algal sources.

The present description refers to a number of documents, their contents of which is herein incorporated by reference in their entirety.

BACKGROUND

Glucaric acid was listed by the US Department of Energy in 2004 as one of the top 12 bio-based chemicals. This dicarboxylic acid could replace phosphoric acid as a builder component in detergents for calcium and magnesium sequestering, and it is also a potential building block for a number of biopolymers including new nylons and hyperbranched polyesters. The global glucaric acid market size was estimated at USD 550.4 million in 2016 on account of increasing demand from detergents, soaps, food ingredients, corrosion inhibitors, and de-icing applications.

Presently, glucaric acid is commercially synthesized as glucarate by the non-selective nitric acid oxidation of glucose with a yield of ca. 40%. This conventional approach as well as recent heterogeneous, metal catalyst methods suffer from low selectivity, increasing the cost for downstream separation of glucaric acid from other organic acid by-products, formed by overoxidation and breaking of C—C bonds. The absence of green technologies for glucaric acid production is one of the reasons for its exclusion from the revised list of new top chemical opportunities from biorefineries (Bozell and Petersen, 2010). Accordingly, considerable investment has been focused on engineering microorganisms, including E. coli (Moon et al., 2009), Pichia pastoris (Liu et al., 2016) and Saccharomyces cerevisiae (Chen et al., 2018), to transform glucose into glucaric acid. However, even when a co-substrate, myo-inositol was added, the yield from glucose remained at 20% after 216 h of fermentation (Chen et al., 2018). Furthermore, this fermentation approach still has problems in downstream separation and extraction, due to the presence of medium components and other metabolites. A recent study demonstrated a cell-free approach to produce glucuronic acid from glucuronoxylan (Lee et al., 2016a), where three enzymes including an endo-xylanase (EC 3.2.1.8), alpha-glucuronidase (EC 3.2.1.139), and uronate dehydrogenase (EC 1.1.1.203) were used in a cocktail or co-localized on a scaffold. The xylanase cleaved glucuronoxylan to various xylo-oligosaccharides, of which some contained 4-O-methyl D-glucuronic acid. The alpha-glucuronidase then removed 4-O-methyl D-glucuronic acid that were attached to the non-reducing end of short xylo-oligosaccharides. The released 4-O-methyl D-glucuronic acid was finally converted to 4-O-methyl D-glucaric acid by the dehydrogenase (Lee, 2016a). Notably, this approach requires a continuous supply of an exogenous cofactor (NAD) and the separation of the 4-O-methyl D-glucaric acid from soluble xylo-oligosaccharides. There thus remains a need for improved processes for the production of glucaric acid.

SUMMARY

The present description relates to the discovery that gluco-oligosaccharide oxidase (GOOX) enzymes have the ability to catalyze the enzymatic conversion of substituted glucuronic acids (such as 4-O-methyl D-glucuronic acid) to their corresponding substituted glucaric acids (such as 4-O-methyl D-glucaric acid). Wild-type GOOX and GOOX variants are shown herein to have striking substrate preference for substituted glucuronic acid over unsubstituted glucuronic acid, with some GOOX variants demonstrating improved performance over the wild-type enzyme for utilizing substituted and/or unsubstituted glucuronic acid as substrates. While previous studies have shown that GOOX can act on oligosaccharides and some monosaccharides (WO/201211431; Foumani et al., 2011), the ability of this enzyme family to utilize glucuronic acid as substrate, and more specifically that the substituted form of glucuronic acid may be the preferred substrate is not believed to have been previously reported. Furthermore, described herein is a simplified two-step enzymic pathway to glucaric acid from a glucuronic acid-substituted polysaccharide such as glucuronoxylan. In general, the pathway involves treating a glucuronic acid-substituted polysaccharide with an enzyme to release the glucuronic acid substituents from its polysaccharide backbone, thereby producing free glucuronic acid and a glucuronic acid-stripped polysaccharide. The free glucuronic acid is then enzymatically converted to glucaric acid via an oxidase or oxidoreductase, such as the GOOX enzymes described herein.

In some aspects, described herein is a process for producing glucaric acid. The process generally comprises: (a) providing a solution comprising dissolved glucuronic acid; (b) providing a recombinant oxidase or oxidoreductase that catalyzes the enzymatic conversion of glucuronic acid to glucaric acid; and (c) contacting the dissolved glucuronic acid with said recombinant oxidase or oxidoreductase under conditions enabling enzymatic conversion of the glucuronic acid to glucaric acid.

In some aspects, described herein is a process for producing glucaric acid from a feedstock, the process comprising: (a) providing a feedstock comprising a glucuronic acid-substituted polysaccharide; (b) enzymatically hydrolyzing the glucuronic acid-substituted polysaccharide to produce glucuronic acid and glucuronic acid-stripped polysaccharide; (c) enzymatically oxidizing the glucuronic acid to glucaric acid; and (d) separating or isolating the glucaric acid from the glucuronic acid-stripped polysaccharide.

In some aspects, described herein a composition comprising substantially enantiomerically pure unsubstituted D-glucaric acid, substituted D-glucaric acid, methyl D-glucaric acid, or 4-O-methyl D-glucaric acid.

In some aspects, described herein is a composition comprising an oxidase or oxidoreductase as described herein, and further comprising: (a) a glucuronic acid as described herein; (b) a glycoside hydrolase as described herein; (c) a catalase as described herein; (d) an unsubstituted or substituted glucaric acid as described herein; or (e) any combination of (a) to (d).

In some aspects, described herein is a recombinant oxidase or oxidoreductase for use in catalyzing the conversion of substituted or unsubstituted glucuronic acid to substituted or unsubstituted glucaric acid, the recombinant oxidase or oxidoreductase being an oxidase or oxidoreductase as described herein.

Abbreviations

AxyAgu115A: GH115 α-glucuronidase from Amphibacillus xylanus; GlcA: D-glucuronic acid; GOOX, gluco-oligosaccharide oxidase; MeGlcA: 4-O-methyl D-glucuronic acid.

General Definitions

Headings, and other identifiers, e.g., (a), (b), (i), (ii), etc., are presented merely for ease of reading the specification and claims. The use of headings or other identifiers in the specification or claims does not necessarily require the steps or elements be performed in alphabetical or numerical order or the order in which they are presented.

The use of the word "a" or "an" when used in conjunction with the term "comprising" in the claims and/or the specification may mean "one" but it is also consistent with the meaning of "one or more", "at least one", and "one or more than one".

The term "about" or "ca." is used to indicate that a value includes the standard deviation of error for the device or method being employed in order to determine the value. In general, the terminology "about" is meant to designate a possible variation of up to 10%. Therefore, a variation of 1, 2, 3, 4, 5, 6, 7, 8, 9 and 10% of a value is included in the term "about". Unless indicated otherwise, use of the term "about" before a range applies to both ends of the range.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used herein, "protein" or "polypeptide", or any protein/polypeptide enzymes described herein, refers to any peptide-linked chain of amino acids, which may or may not comprise any type of modification (e.g., chemical or post-translational modifications such as acetylation, phosphorylation, glycosylation, sulfatation, sumoylation, prenylation, ubiquitination, etc.). For further clarity, protein/polypeptide/enzyme modifications are envisaged so long as the modification does not destroy the desired enzymatic activity (e.g., conversion of glucuronic acid to glucaric acid, or cleavage of glucuronic acid from glucuronoxylan). In some embodiments, the proteins/polypeptides/enzymes described herein may be synthesized with one or more D- or L-amino acids, to the extent that the modification does not destroy the desired enzymatic activity.

As used herein, the term "recombinant" in the context of enzymes and polypeptides described herein, refer to those produced via recombinant DNA technology. In some embodiments, the recombinant enzymes and polypeptides described herein may be structurally different, or may be present in a form (e.g., concentration, or purity) that would not be found in nature.

Other objects, advantages and features of the present description will become more apparent upon reading of the following non-restrictive description of specific embodiments thereof, given by way of example only with reference to the accompanying drawings.

BRIEF DESCRIPTION OF THE DRAWINGS

In the appended drawings:

FIG. 1: Proposed two-enzyme pathway for 4-O-methyl glucaric acid production from glucuronoxylan.

5

Figure 13A:
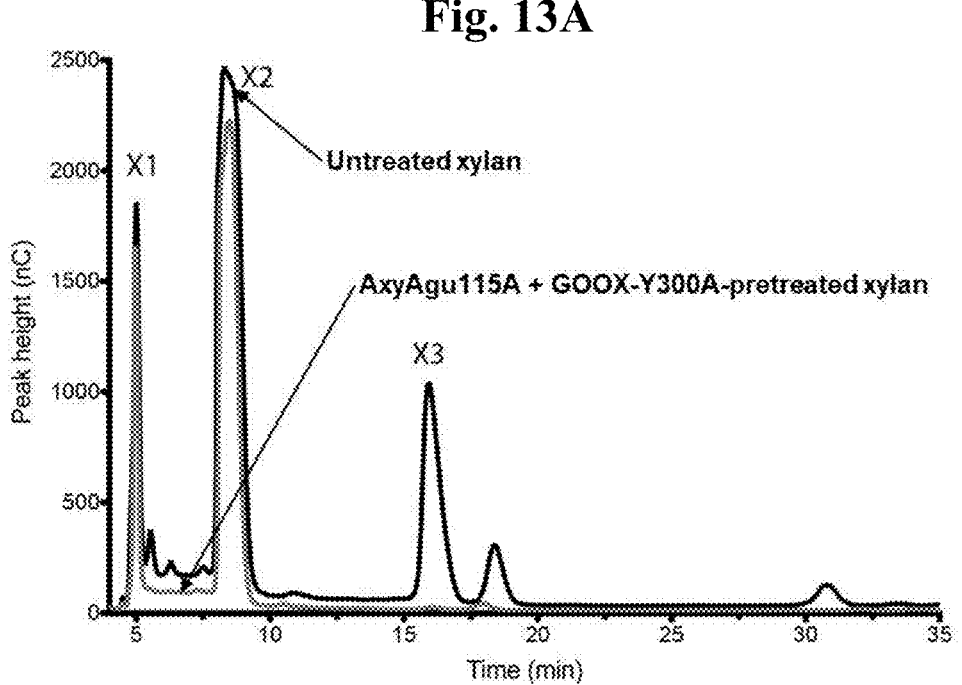
FIG. 13: HPAEC-PAD analysis for xylanase digestion of untreated xylan (black), as well as AxyAgu115A.
Figure 13B:
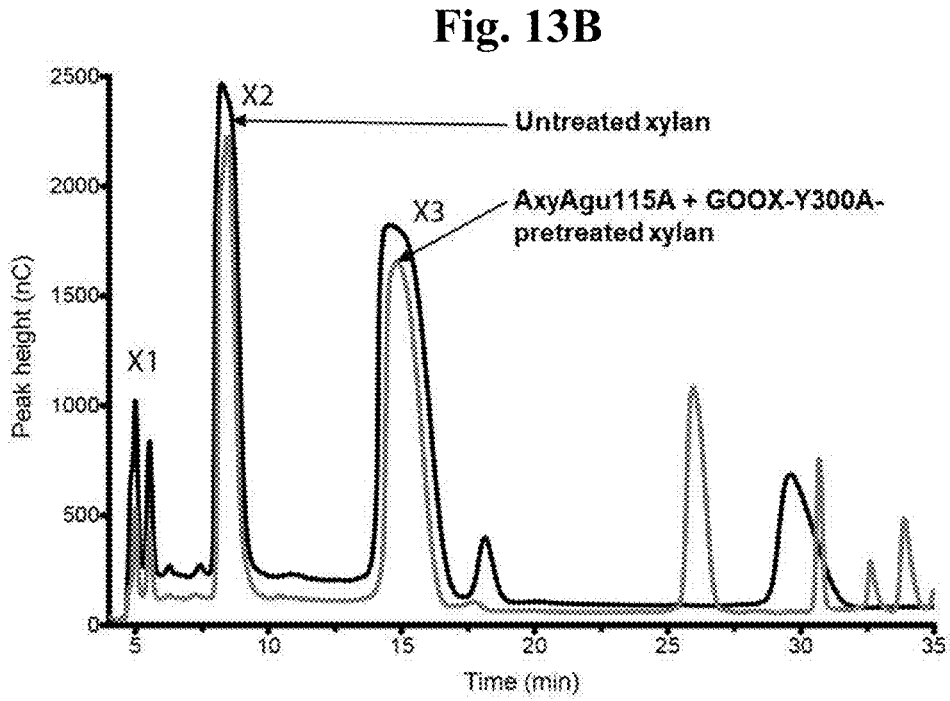

GOOX-Y300A-pretreated xylan (red). Xylan samples were either treated with Xyn10B (FIG. 13A) or Xyn11A (FIG. 13B); X1, X2 and X3 are xylose, xylobiose and xylotriose correspondingly.

SEQUENCE LISTING

This application contains a Sequence Listing in a computer readable form created on May 15, 2020 having a size of about 28 kb. The computer readable form is incorporated herein by reference.

| SEQ ID NO: | Description |
| --- | --- |
| 1 | Wild-type GOOX from *Sarocladium strictum* |
| 2 | FAD-binding domain of SEQ ID NO: 1 |
| 3 | Substrate-binding domain of SEQ ID NO: 1 |
| 4 | AxyAgu115A |
| 5 | SdeAgu115A |

DETAILED DESCRIPTION

The present description relates to the discovery that gluco-oligosaccharide oxidase (GOOX) enzymes have the ability to catalyze the enzymatic conversion of substituted glucuronic acids (such as 4-O-methyl D-glucuronic acid) to their corresponding substituted glucaric acids (such as 4-O-methyl D-glucaric acid). Wild-type GOOX and GOOX variants are shown herein to have striking substrate preference for substituted glucuronic acid over unsubstituted glucuronic acid, with some GOOX variants demonstrating improved performance over the wild-type enzyme for utilizing substituted and/or unsubstituted glucuronic acid as substrates (see Example 3). While previous studies have shown that wild-type GOOX or some GOOX variants can act on oligosaccharides and some monosaccharides (WO/201211431; Foumani et al., 2011), the ability of this enzyme family to utilize glucuronic acid as substrate, and more specifically that the substituted form of glucuronic acid may be the preferred substrate is not believed to have been previously reported.

In one aspect, described herein is a process for producing glucaric acid from glucuronic acid. The process generally involves providing a solution comprising dissolved glucuronic acid and a recombinant oxidase or oxidoreductase that catalyzes the enzymatic conversion of glucuronic acid to glucaric acid. The dissolved glucuronic acid is allowed to contact the oxidase or oxidoreductase under conditions enabling enzymatic conversion of the glucuronic acid to glucaric acid.

As used herein, the expressions "glucuronic acid" and "glucaric acid" generally include unsubstituted and substituted forms of the acids (e.g., substituted glucuronic acid and/or substituted glucaric acid, 4-O-substituted glucuronic acid and/or 4-O-substituted glucaric acid, methyl glucuronic acid and/or methyl glucaric acid, or more specifically 4-O-methyl glucuronic acid and/or 4-O-methyl glucaric acid, or even more specifically 4-O-methyl D-glucuronic acid and/or 4-O-methyl D-glucaric acid), as well as salts thereof, to the extent that the acids are substrates or products of the oxidase or oxidoreductase as described herein. For greater clarity, the expressions "methyl glucuronic acid" and/or "methyl glucaric acid" comprise methyl-substituted forms of the acids, such as 4-O-methyl glucuronic acid and/or 4-O-methyl glucaric acid, or even more specifically 4-O-methyl D-glucuronic acid and/or 4-O-methyl D-glucaric acid).

In some implementations, the oxidase or oxidoreductase may be an enzyme of class E.C. 1.1.99 that catalyzes the enzymatic conversion of glucuronic acid to glucaric acid. In some implementations, the oxidase or oxidoreductase may be an enzyme of class E.C. 1.1.99 that catalyzes the enzymatic conversion of glucuronic acid to glucaric acid, wherein the oxidase or oxidoreductase has higher substrate specificity for substituted glucuronic acid as compared to unsubstituted glucuronic acid (e.g., higher specificity for 4-O-methyl glucuronic acid as compared to unsubstituted glucuronic acid).

In some implementations, the oxidase or oxidoreductase may be a gluco-oligosaccharide oxidase (GOOX) or variant thereof, such as a GOOX of class E.C. 1.1.99.B3 (e.g., a variant of the wild-type GOOX from Sarocladium strictum set forth in SEQ ID NO: 1). In some implementations, the GOOX may comprise an amino acid sequence having at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% identity to SEQ ID NO: 1.

In some implementations, the GOOX variants described herein may comprise a flavin adenine dinucleotide (FAD)-binding domain comprising an amino acid sequence having at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% identity to SEQ ID NO: 2, operably linked to a substrate-binding domain comprising an amino acid sequence having at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% identity to SEQ ID NO: 3.

In some implementations, the GOOX variant may comprise one or more amino acid differences as compared to SEQ ID NO: 1 at residue positions 207 to 474 (substrate-binding domain), wherein the variant exhibits increased substrate specificity to substituted or unsubstituted glucuronic acid as compared to a corresponding GOOX polypeptide (e.g., the GOOX of SEQ ID NO: 1) lacking said amino acid differences. In some implementations, the GOOX is a GOOX variant comprising one or more differences as compared to SEQ ID NO: 1 at least at residue position 300, wherein the GOOX variant catalyzes the conversion of glucuronic acid to glucaric acid. In some implementations, the GOOX is a GOOX variant comprising one or more differences as compared to SEQ ID NO: 1 at residue position 300, 72, 247, 314, 351, 353, 388, or any combination thereof, preferably wherein said GOOX variant exhibits improved activity utilizing substituted or unsubstituted glucuronic acid as substrate over the GOOX of SEQ ID NO: 1. In some implementations, the GOOX is a GOOX variant comprising one or more differences as compared to SEQ ID NO: 1, wherein the GOOX variant catalyzes the conversion of methyl glucuronic acid to methyl glucaric acid. In some implementations, the GOOX is a GOOX variant comprising one or more differences as compared to SEQ ID NO: 1, wherein the GOOX variant has higher substrate preference or specificity for substituted glucuronic acid (e.g., methyl glucuronic acid) as compared to the corresponding unsubstituted glucuronic acid (e.g., as shown in Example 3). In some implementations, the GOOX variants described herein may comprise 300A relative to the amino acid residue numbering of SEQ ID NO: 1. In some implementations, the GOOX variants described herein may comprise 300A, 72F, 247A, 314A, 351A, 353A or 353N, 388S, or any combination thereof relative to the amino acid positioning of SEQ ID NO: 1. In some implementations, the GOOX variants described herein may comprise two or more amino acid differences as compared to SEQ ID NO: 1 at residue position 300 and at residue position 72, 247, 314, 351, 353, 388, or any combination thereof, preferably wherein said GOOX variant exhibits improved activity utilizing substituted or unsubstituted glucuronic acid as substrate over the GOOX of SEQ ID NO: 1. In some implementations, the GOOX variants described herein may comprise 300A and 72F, 247A, 314A, 351A, 353A or 353N, 388S, or any combination thereof relative to the amino acid positioning of SEQ ID NO: 1. In some implementations, the GOOX is a variant of a Sarocladium strictum (previously known as *Acremonium* strictum) GOOX polypeptide, wherein the Sarocladium strictum GOOX polypeptide comprises, or is defined by, an amino acid sequence that has at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% identity to SEQ ID NO: 1.

Figure 1:
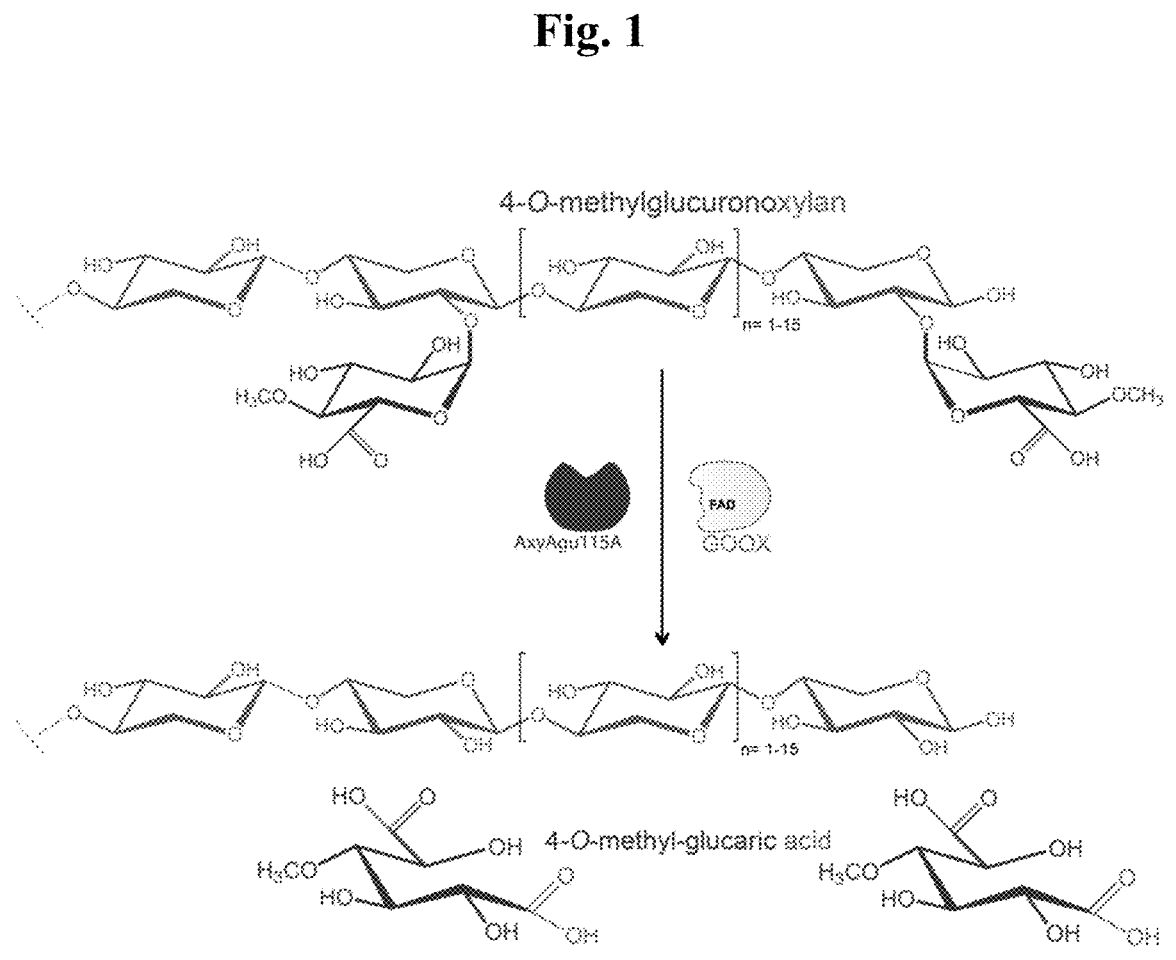

In some implementations, one or more the oxidase or oxidoreductase (e.g., GOOX enzymes) described herein may be immobilized to a solid support, particle, or matrix. In some implementations, the oxidase or oxidoreductase enzymes (e.g., GOOX enzymes) described herein catalyze the oxidation of glucuronic acid to glucaric acid in the absence of exogenous cofactor supplementation, such as NAD. For greater clarity, "exogenous cofactor" refers to the glucuronic acid to glucaric acid conversion via a dehydrogenase as described in Lee et al., 2016a, which requires a continuous supply of NAD to be added to the reaction solution, but excludes the endogenous FAD cofactor present in GOOX (see FIG. 1).

Figure 9:
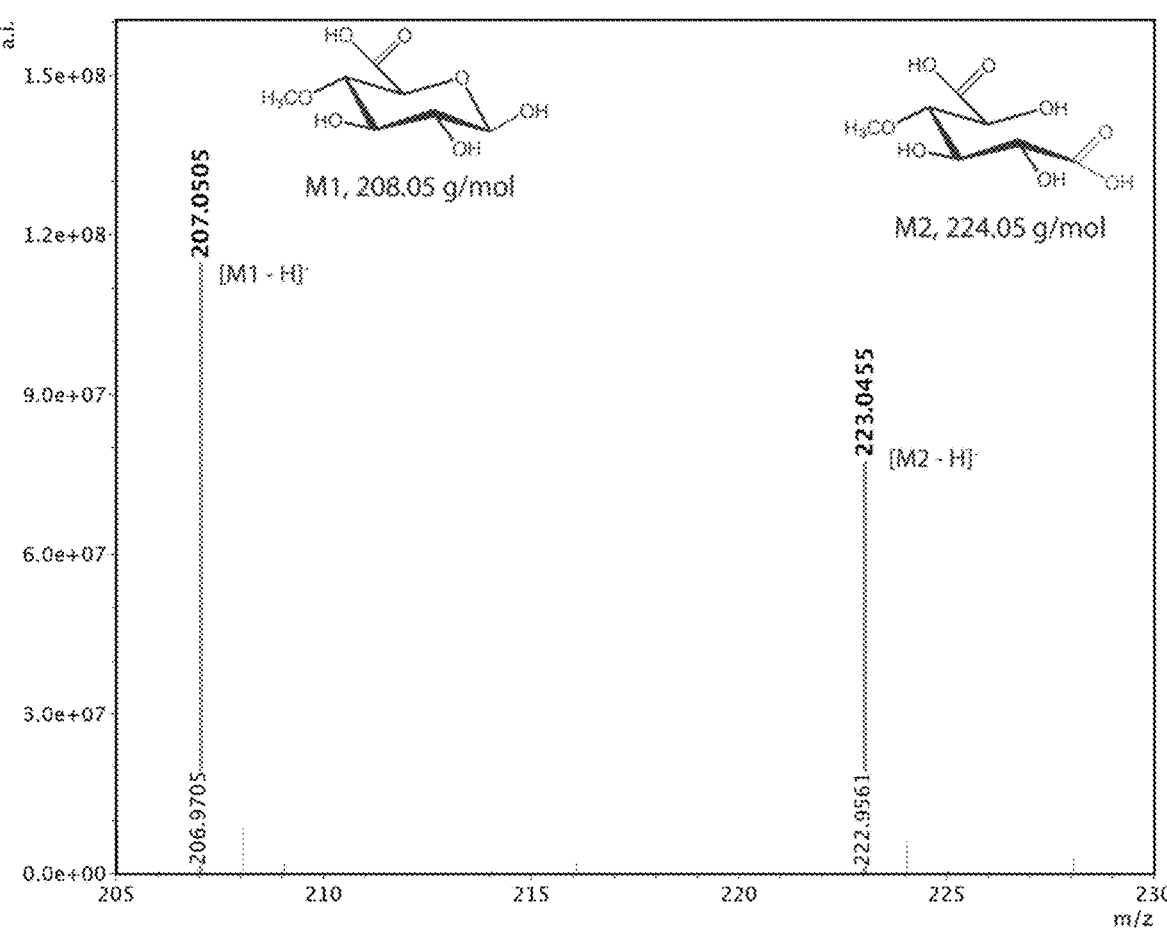
FIG. 9: NSI-MS spectrum for the formation of 4-O-methyl D-glucaric acid (224.05 g/mol) by GOOX-Y300A. The reaction was carried in 300 mM Tris buffer pH 8.0 with 60 mM MeGlcA (208.05 g/mol).

In some implementations, processes as described herein comprising the enzymatic conversion of the glucuronic acid to glucaric acid may occur in a buffer having an ionic strength of at least 100, 150, 200, 250, 300, 350, 400, 450, or 500 mM. In some implementations, the higher ionic strength increases the molar ratio of glucaric acid to glucuronic acid produced by the process, as compared to a buffer having a lower ionic strength (e.g., less than 100 mM or less than 50 mM). In this regard, Example 3 and FIG. 9 show that oxidation of glucuronic acid to glucaric acid by GOOX was improved when the ionic strength of the buffer used was increased to 300 mM. In some implementations, processes as described herein comprising the enzymatic conversion of the glucuronic acid to glucaric acid may occur in a buffer having an ionic strength of $C^{max}$, wherein $C^{max}$ is the ionic strength at which the molar ratio of glucaric acid to glucuronic acid produced by the process is highest.

In some implementations, processes described herein comprising the enzymatic conversion of the glucuronic acid to glucaric acid may advantageously occur in a buffer having an alkaline pH (e.g., above 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.1, 10.2, 10.3, 10.4, 10.5; or from 7.5 to 11, 8 to 11, 8.5 to 11, 9 to 11, 9.5 to 11, or 9.5 to 10.5). In this regard, enzymes described herein (e.g., GOOX and alpha-glucuronidase from glycoside hydrolase family) are shown to prefer alkaline conditions. Furthermore, $H_2O_2$ that may be generated as a by-product from the oxidation of glucuronic acid to glucaric acid by the oxidase or oxidoreductase described herein (e.g., GOOX) is less stable in alkaline conditions, facilitating its inactivation and reducing its potential inhibitory or detrimental effects to the process. Furthermore, alkaline conditions are associated with other advantages, such as the ability to increase polysaccharide feedstock loading (e.g., to greater than 1%, 2%, 3%, 4%, 5%, 6%, 7%, 8%, 9%, or 10% w/v), and to reduce the presence of multiple lactone forms of glucaric acid (Hong et al., 2016) that could hinder product recovery.

In some implementations, processes described herein comprising the enzymatic conversion of the glucuronic acid to glucaric acid may advantageously occur at a temperature above 37° C., such as between 38° C. and 45° C., 38° C. and 44° C., 38° C. and 43° C., 38° C. and 42° C., 39° C. to 41° C., or about 40° C. $H_2O_2$ that may be generated as a by-product from the oxidation of glucuronic acid to glucaric acid by the oxidase or oxidoreductase described herein (e.g., GOOX) is less stable at higher temperatures, facilitating its inactivation and reducing its potential inhibitory or detrimental effects.

In some implementations, processes described herein comprising the enzymatic conversion of the glucuronic acid to glucaric acid may advantageously occur in the absence of exogenous continuous cofactor supplementation (e.g., NAD supplementation), which would considerably increase production costs.

In some implementations, processes described herein may utilize glucuronic acid obtained or produced by any suitable means (e.g., enzymatically or chemically). In some implementations, processes described herein may utilize substituted glucuronic acid, which is enzymatically converted to the corresponding substituted glucaric acid by the recombinant oxidase or oxidoreductase described herein. In some implementations, processes described herein may utilize methyl glucuronic acid (e.g., 4-O-methyl glucuronic acid), which is enzymatically converted to methyl glucaric acid (e.g., 4-O-methyl glucaric acid) by the recombinant oxidase or oxidoreductase described herein. In some implementations, processes described herein may utilize substantially enantiomerically pure D-glucuronic acid or methyl D-glucuronic acid, which is enzymatically converted to substantially enantiomerically pure methyl D-glucaric acid (e.g., 4-O-methyl D-glucaric acid) by the recombinant oxidase or oxidoreductase described herein. As used herein, "substantially enantiomerically pure" generally refers to a level of purity such that the presence of undesired enantiomeric forms is negligible and/or undetectable, or not present in sufficient quality to be of functional significance for the intended use (e.g., polymer/nylon synthesis from D-glucaric acid or 4-O-methyl D-glucaric acid). In some embodiments, "substantially enantiomerically pure" refer to a purity of at least 95%, 96%, 97%, 98%, 99%, or 99.5% by weight.

In some implementations, processes described herein may utilize glucuronic acid obtained (released from) from enzymatic treatment of a glucuronic acid-substituted polysaccharide, thereby producing released (free) glucuronic acid and glucuronic acid-stripped polysaccharide. As used herein, the expression "glucuronic acid-substituted polysaccharide" refers to any polysaccharide containing glucuronic acid or the substituted form of glucuronic acid (e.g., 4-O-methyl-glucuronic acid), including glucuronoxylans from hardwood (deciduous) trees, arabinoglucuronoxylans from softwood (coniferous) trees, glucuronoarabinoxylan from agricultural fibre, and ulvan from green algae. In some implementations, the glucuronic acid-substituted polysaccharide may be or comprise glucuronic acid-substituted xylan, glucuronic acid-substituted arabinoxylan, and/or glucuronic acid-substituted ulvan. More specifically in some implementations, the glucuronic acid-substituted polysaccharide may be or comprise methyl-glucuronoxylan, arabinoglucuronoxylan, glucuronoarabinoxylan, or ulvan. In more specific implementations, processes described herein may utilize glucuronic acid obtained (released from) from enzymatic treatment of glucuronoxylan to produce glucuronic acid and stripped xylan (Example 2 and FIGS. 3-5).

In some implementations, the glucuronic acid may be obtained from enzymatic treatment of the glucuronic acid-substituted polysaccharide with a glycoside hydrolase. In some implementations, the glycoside hydrolase catalyzes the release of glucuronic acid from glucuronoxylan, preferably under alkaline conditions. In some implementations, the glycoside hydrolase may be a glucuronidase. As used herein, the expression "glucuronidase" refers to either alpha-glucuronidase and/or beta-glucuronidase that removes glucuronic acid with either alpha linkages and/or beta linkages from glucuronic acid-substituted. In some implementations, the glycoside hydrolase may be a glucuronidase belonging to the glycoside hydrolase (GH) family GH2, GH67 or GH115. Such enzymes generally have the ability to release glucuronic acid from glucuronoxylan, although glucuronidases (e.g., alpha-glucuronidase) from family GH115 are expected to perform better than glucuronidases from family GH67.

Figure 3:
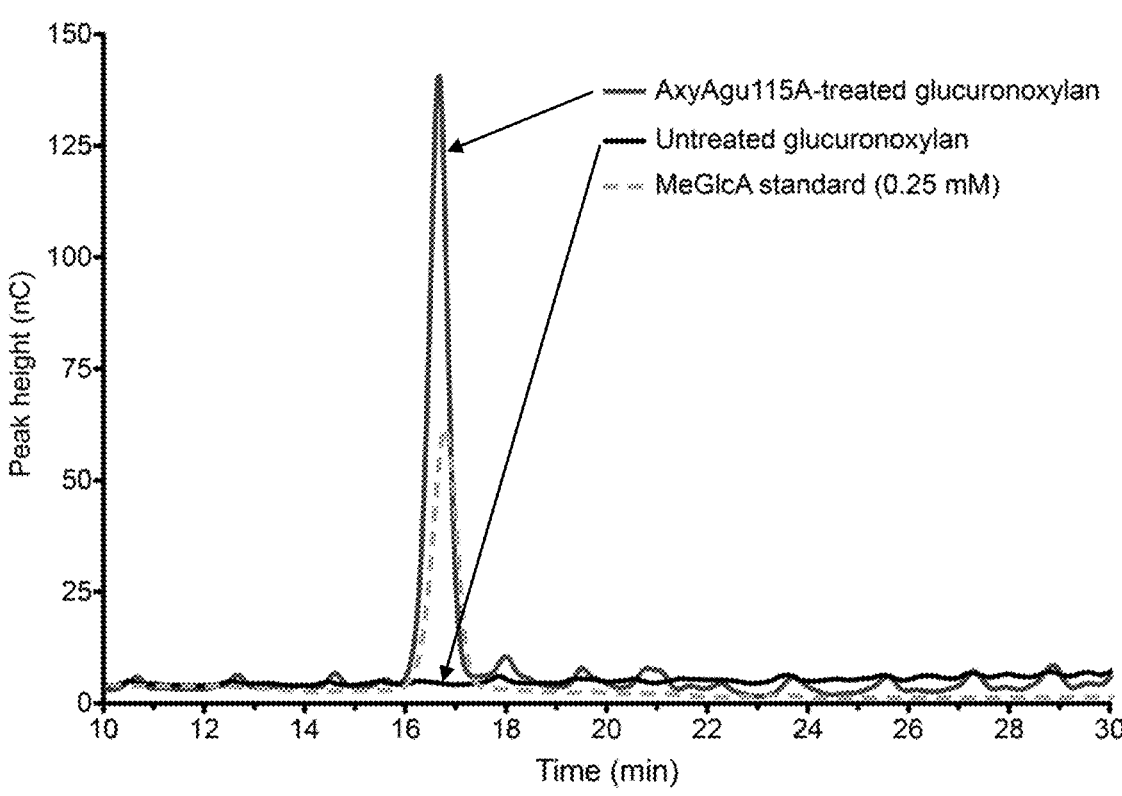
FIG. 3: HPAEC-PAD analysis of AxyAgu115A action on glucuronoxylan. The presence of 4-O-methyl D-glucuronic acid (MeGlcA) was detected in the treatment of glucuronoxylan with AxyAgu115A (red line), not in the untreated glucuronoxylan sample (black line). 0.25 mM MeGlcA (grey, dashed line) was included as the standard.
Figure 4:
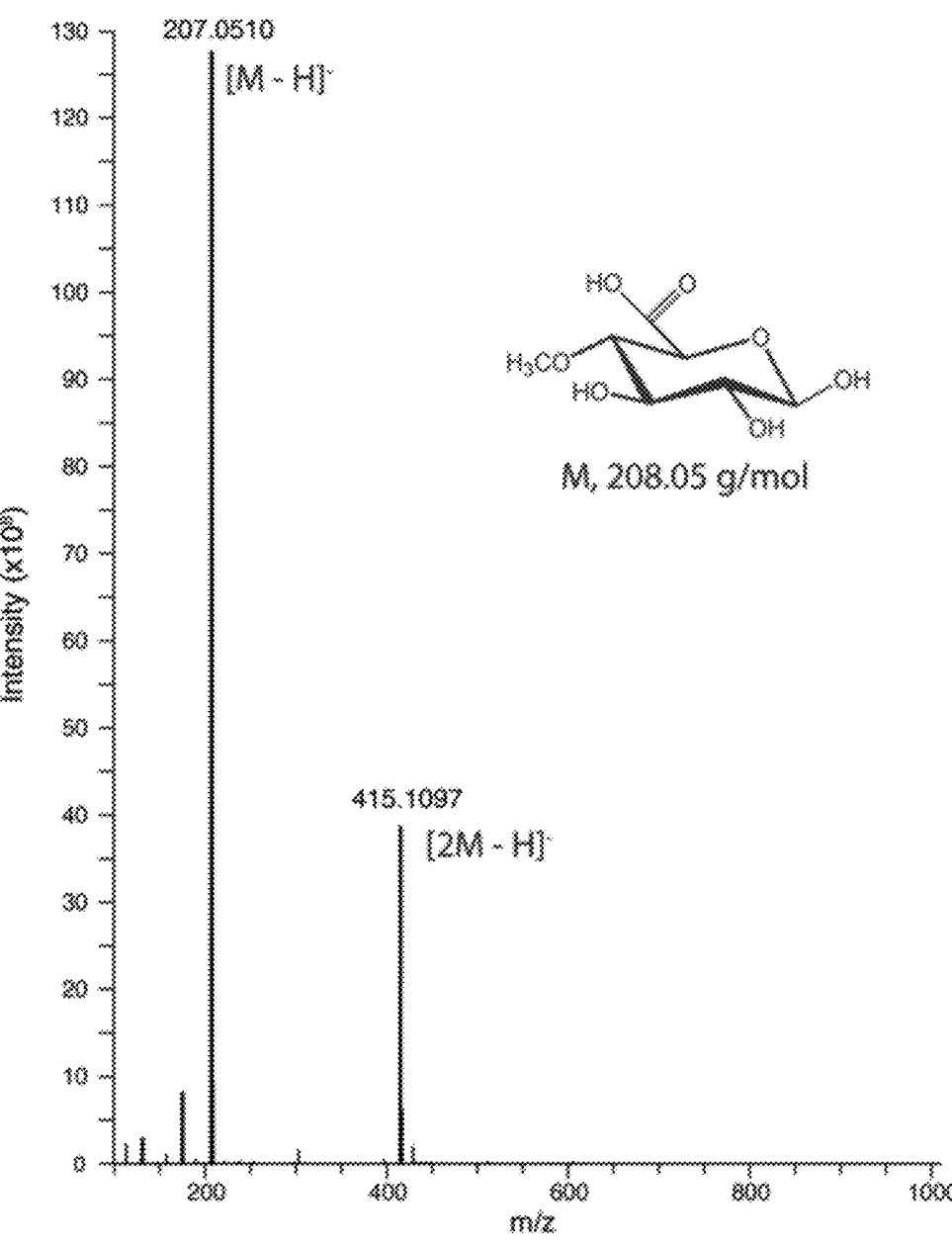
FIG. 4: Nanospray Ionization Ion-trap Mass Spectrometry (NSI-MS) spectrum of released MeGlcA (208.05 g/mol) by AxyAgu115A. Samples in 50% methanol were injected in a negative mode and the spectrum was recorded from 100 m/z to 1,000 m/z.
Figure 5:
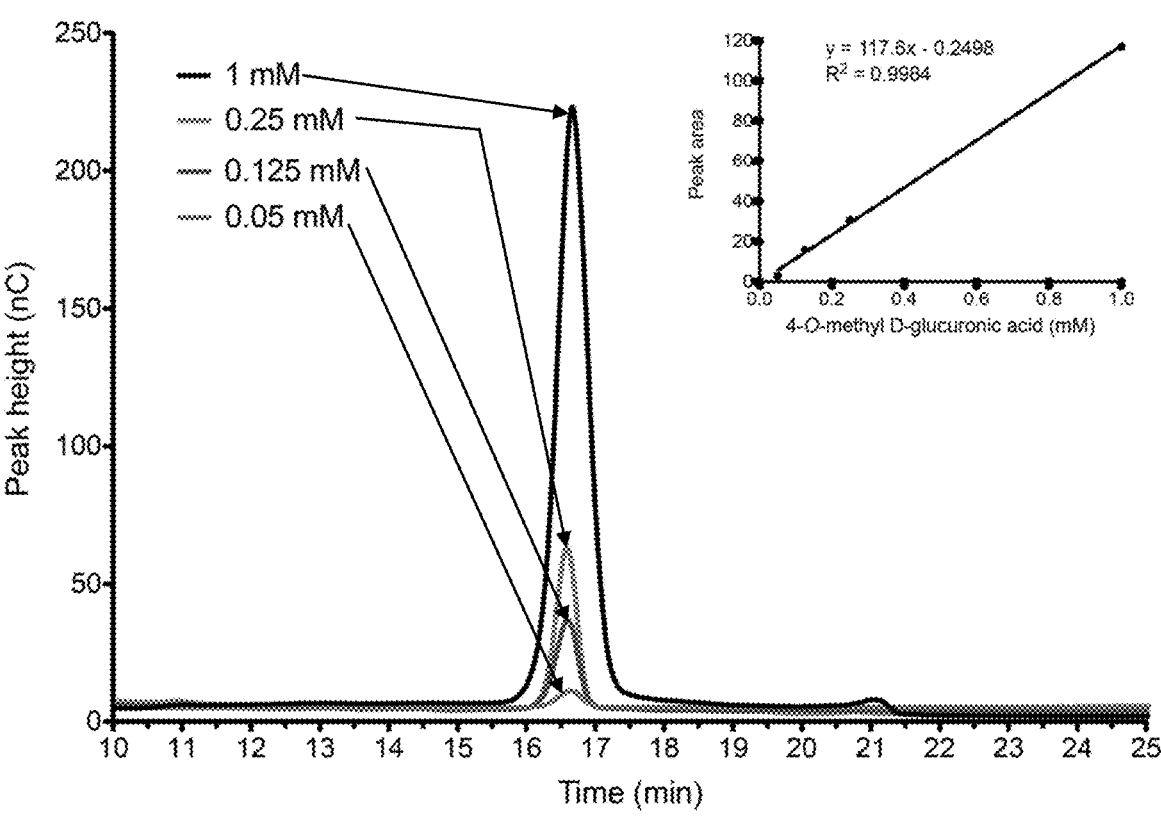
FIG. 5: MeGlcA (0.05 mM-1 mM) standard curve by HPAEC-PAD.

In some implementations, processes described herein may utilize glucuronic acid obtained (released from) from enzymatic treatment of glucuronoxylan with a glucuronidase (e.g., an alpha-glucuronidase) from glycoside hydrolase family GH115 (Example 2 and FIGS. 3-5).

In some implementations, the alpha-glucuronidase may be a GH115 alpha-glucuronidase from Amphibacillus xylanus (AxyAgu115A) (Yan et al., 2017), or a variant thereof, or another glucuronidase that catalyzes the release of glucuronic acid from glucuronoxylan. In some implementations, the AxyAgu115A variant polypeptide may comprise, or be defined by, an amino acid sequence that has at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% identity to SEQ ID NO: 4.

In some implementations, the alpha-glucuronidase may be a GH115 alpha-glucuronidase from SdeAgu115A (Wang et al., 2016), or a variant thereof, or another glucuronidase that catalyzes the release of glucuronic acid from glucuronoxylan. In some implementations, the SdeAgu115A variant polypeptide may comprise, or be defined by, an amino acid sequence that has at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% identity to SEQ ID NO: 5.

In some implementations, the enzymatic treatment of glucuronic acid-substituted polysaccharide to release the glucuronic acid and the conversion of glucuronic acid to glucaric acid by the oxidase or oxidoreductase may advantageously be performed in the same reaction vessel (i.e., a one-pot reaction), preferably at alkaline pH (such as from 7.5 toll, 8 to 11, 8.5 toll, 9 to 11, 9.5 to 11, or 9.5 to 10.5). In some implementations, both enzymatic steps may be performed simultaneously or sequentially. Sequential two-step processes comprise the enzymatic treatment of glucuronic acid-substituted polysaccharide to release the glucuronic acid, followed by the conversion of glucuronic acid to glucaric acid by the oxidase or oxidoreductase (Example 4 and FIG. 10). Such an approach may be advantageous, as peroxide (e.g., $H_2O_2$) generated as a by-product of the oxidation of glucuronic acid to glucaric acid may inhibit or interfere with other reaction components, such as the activity and/or stability of the glucuronidase. In some implementations, the processes described herein may be carried under conditions that minimize or reduce the level of peroxide to levels that do not substantially negative affect the enzymatic cleavage of glucuronic acid from the glucuronic acid-substituted polysaccharide (e.g., alkaline pH, elevated temperature, lighting conditions). In some implementations, the processes described herein may comprise a catalase that catalyzes the breakdown hydrogen peroxide generated by the oxidase or oxidoreductase.

In some implementations, at least a fraction of one or more of the enzymes described herein (e.g., glycoside hydrolase, glucuronidase, oxidase or oxidoreductase, and/or catalase) may be immobilized to a solid support, particle, or matrix. In some implementations, at least a fraction of one or more of the enzymes described herein (e.g., glycoside hydrolase, glucuronidase, oxidase or oxidoreductase, and/or catalase) may be free in the reaction solution.

Figures 12, 12A, 12B, 12C, 12D:
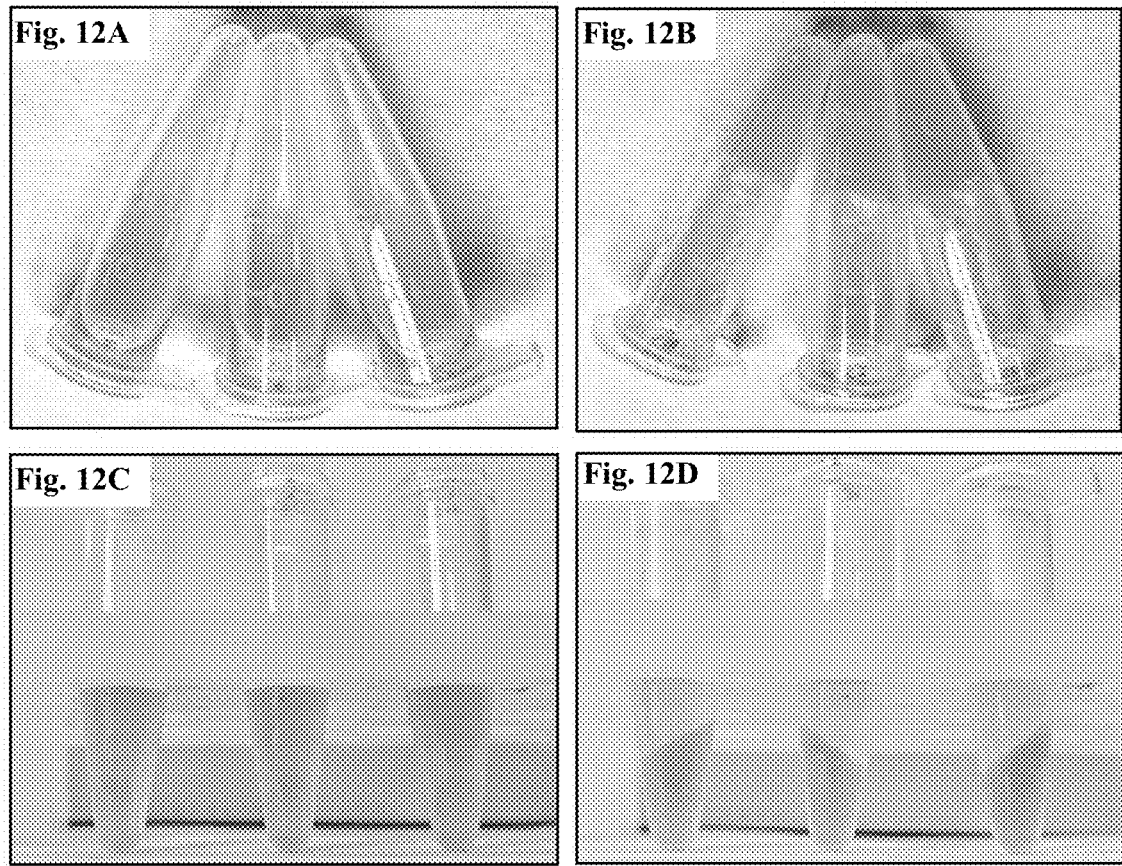
FIG. 12: Isolation of xylan after AxyAgu115 and GOOX-Y300A treatment. Untreated glucuronoxylan remained soluble before (FIG. 12A) and after (FIG. 12C) centrifugation; however, hydrogel-like material was formed (FIG. 12B) in the reaction incubated with the two enzymes, and it was separated out by centrifugation (FIG. 12D).

In some implementations, the process described here may comprise isolating or purifying the glucuronic acid-stripped polysaccharide (e.g., glucuronic acid-stripped xylan) produced the enzymatic treatment of the glucuronic acid-substituted polysaccharide (e.g., glucuronoxylan) to cleave glucuronic acid. In this regard, Example 5 and FIG. 12 show that the resulting xylan pursuant to the two-step processed described herein, is hydrogel-like, facilitating its separation from the reaction. Xylanases were able to hydrolyze this pre-treated xylan to release xylose and xylo-oligosaccharides (FIG. 13).

In some aspects, described herein is a process for producing glucaric acid from a hemicellulose feedstock. The process comprises (a) providing a feedstock comprising a glucuronic acid-substituted polysaccharide; (b) enzymatically hydrolyzing the glucuronic acid-substituted polysaccharide to produce glucuronic acid and glucuronic acid-stripped polysaccharide; (c) enzymatically oxidizing the glucuronic acid to glucaric acid; and (d) separating or isolating the glucaric acid from the glucuronic acid-stripped polysaccharide. In some implementations, steps (b) and/or (c) are as described herein.

In some aspects, described herein a composition comprising substantially enantiomerically pure unsubstituted D-glucaric acid, substituted D-glucaric acid, methyl D-glucaric acid, or 4-O-methyl D-glucaric acid. In some implementations, the composition may be produced by a process as described herein. In some implementations, the unsubstituted D-glucaric acid, substituted D-glucaric acid, methyl D-glucaric acid, or 4-O-methyl D-glucaric acid may be comprised as a substantially single acid form (as opposed as an oxidized form such as 1,5-lactone), which is favored by alkaline conditions of the processes described herein. In some implementations, the glucaric acids produced by the processed described herein (e.g., unsubstituted D-glucaric acid, substituted D-glucaric acid, methyl D-glucaric acid, or 4-O-methyl D-glucaric acid) may be employed in the production of (bio-based) nylons having novel or unique properties. Furthermore, the methylated form of glucaric acid could bring additional functional properties to the chemical, including higher compatibility with surfactants in detergents and hydrophobic biopolymers (Rorrer et al., 2016). Methyl groups of monomers contributed to the molecular architecture and subsequent properties of their derived biopolymers (Rorrer et al., 2016).

In some implementations, the glucuronoxylan utilised in the processes described herein may be obtained from a xylan waste stream (e.g., corn fibre hemicelluloses). Ethanol production from corn grain generates a protein-rich co-product that is also typically used as an animal feed. In addition to this, a corn fibre stream is generated that is currently underutilized. Roughly 30% of corn fibre recovered from corn ethanol plants is xylan, which could be a good source of glucuronoxylan for the glucaric acid production processes described herein. In turn, the stripped xylan (which may be of higher uniformity than other xylan sources) that is recovered may be utilized as rheology modifiers, coatings, packaging films, and food additives.

In some implementations, the process can include pre-treatment or preparation steps to produce a feedstock that includes glucuronoxylan (or other glucuronic acid-substituted polysaccharide) and/or glucuronic acid for conversion into end products. The pre-treatment steps can involve the processing of plant-based biomass to form a solution that contains desired levels of glucuronic acid-substituted polysaccharide, glucuronoxylan, glucuronic acid, or other compounds that include glucuronic acid groups. For example, as mentioned above, ethanol production from corn grain can generate corn fibre that is suitable for use as a source of glucuronoxylan. The corn fibres can be dissolved in water at desired pH and temperature levels, with or without prior grinding, to produce a feedstock material that can be used for enzymatic conversion. Prior to enzymatic conversion, the feedstock material can then be pre-treated by separating certain undesirable compounds, such as suspended solids. In another example, the source of glucuronic acid-substituted polysaccharide, glucuronoxylan and/or glucuronic acid is from biomass, such as softwood or hardwood, used in the pulp and paper industry. When biomass is cooked using hot water or steam extraction without the use of harsh chemicals, the resulting cooked slurry can be separated to form a pulp fibre stream for paper production and an extraction solution rich in hemicellulose. This extraction solution can be used as feedstock for enzymatic conversion as described herein. The extraction solution can also be pre-treated by filtration or other solids-removal methods to remove pulp fibres or other suspended solids. The temperature and/or pH of the extraction solution can also be adjusted, depending on the extraction procedure. It should be noted that the pre-treatment can be adapted depending on the source of glucuronic acid to be processed and converted into glucaric acid. For instance, when glucuronoxylan is a source, then the feedstock can be prepared for to facilitate enzymatic conversion into glucuronic acid and stripped xylan. When another compound is a source of the glucuronic acid groups bound to other groups, then the feedstock can be pre-treated appropriately so that the source can be converted into glucuronic acid.

In some implementations, the feedstock including compounds that include glucuronic acid groups is subjected to a first conversion step to produce a first output material that includes glucuronic acid that has been cleaved from the other groups. In the case of glucuronoxylan, the glucuronic acid groups and thus separated from the xylan groups, and this conversion can be done enzymatically as described herein. Depending on the starting compounds from which the glucuronic acid groups are to be cleaved, the first conversion step can be performed by enzymatic and/or chemical conversion. The first output material can then be subjected to a second conversion step that includes enzymatic conversion of the glucuronic acid groups to produce a second output material that includes glucaric acid. The second output material can then be subjected to separation to remove certain target compounds, such as the glucaric acid and other compounds cleaved from the initial compounds that included glucuronic acid groups. In the case of glucuronoxylan as a starting material, the stripped xylan can be present in the second output material and can be separated to obtain a co-product. Alternatively, the first output material can be subjected to one or more separation steps to remove desired compounds, e.g., stripped xylan, and then the separated glucuronic acid can be subjected to enzymatic conversion to produce glucaric acid. In some cases, the first and second conversion steps are performed sequentially, which may be in a same vessel or two separate vessels. In addition, depending on the target compounds to be separated, various separation techniques can be used (e.g., centrifugation).

In some aspects, described herein is a composition comprising an oxidase or oxidoreductase as described herein and further comprising: (a) a glucuronic acid as described herein; (b) a glycoside hydrolase as described herein; (c) the catalase as described herein; (d) the unsubstituted or substituted glucaric acid as described herein; or (e) any combination of (a) to (d).

In some aspects, described herein is a recombinant oxidase or oxidoreductase for use in catalyzing the conversion of substituted or unsubstituted glucuronic acid to substituted or unsubstituted glucaric acid, the recombinant oxidase or oxidoreductase being an oxidase or oxidoreductase as described herein. In some implementations, the recombinant oxidase or oxidoreductase is for use in a process as defined herein.

Items

1. A process for producing glucaric acid, the process comprising: providing a solution comprising dissolved glucuronic acid; providing a recombinant oxidase or oxidoreductase that catalyzes the enzymatic conversion of glucuronic acid to glucaric acid; and contacting the dissolved glucuronic acid with said recombinant oxidase or oxidoreductase under conditions enabling enzymatic conversion of the glucuronic acid to glucaric acid.

2. The process of item 1, wherein the recombinant oxidase or oxidoreductase that catalyzes the enzymatic conversion of glucuronic acid to glucaric acid belongs to class E.C. 1.1.99.

3. The process of item 1 or 2, wherein the recombinant oxidase or oxidoreductase has higher substrate specificity for substituted glucuronic acid as compared to unsubstituted glucuronic acid.

4. The process of any one of items 1 to 3, wherein the oxidase or oxidoreductase is a gluco-oligosaccharide oxidase (GOOX) variant, such as of class E.C. 1.1.99.B3, that catalyzes the oxidation of glucuronic acid to glucaric acid.

5. The process of item 4, wherein the GOOX variant has higher substrate specificity for glucuronic acid as compared to the GOOX of SEQ ID NO: 1.

6. The process of any one of items 1 to 5, wherein the oxidase or oxidoreductase:

(i) is a GOOX variant comprising an FAD-binding domain comprising an amino acid sequence having at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% identity to SEQ ID NO: 2, operably linked to a substrate binding domain comprising an amino acid sequence having at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% identity to SEQ ID NO: 3;

(ii) is the GOOX variant of (i), further comprising one or more amino acid differences as compared to SEQ ID NO: 1 at residue positions 207 to 474, wherein the variant exhibits increased substrate specificity for substituted or unsubstituted glucuronic acid as compared to a corresponding GOOX polypeptide lacking said one or more amino acid differences;

(iii) is a GOOX variant comprising one or more amino acid differences as compared to SEQ ID NO: 1 at residue position 300, 72, 247, 314, 351, 353, 388, or any combination thereof, preferably wherein said GOOX variant exhibits improved activity utilizing substituted or unsubstituted glucuronic acid as substrate over the GOOX of SEQ ID NO: 1;

(iv) is a GOOX variant comprising 300A, 72F, 247A, 314A, 351A, 353A or 353N, 388S, or any combination thereof relative to the amino acid positioning of SEQ ID NO: 1;

(v) is a GOOX variant comprising two or more amino acid differences as compared to SEQ ID NO: 1 at residue position 300 and at residue position 72, 247, 314, 351, 353, 388, or any combination thereof;

(vi) is a GOOX variant comprising 300A and 72F, 247A, 314A, 351A, 353A or 353N, 388S, or any combination thereof relative to the amino acid positioning of SEQ ID NO: 1;

(vii) is a GOOX variant comprising an amino acid sequence having at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% identity to SEQ ID NO: 1;

(viii) is a variant of a Sarocladium strictum GOOX polypeptide, said Sarocladium strictum GOOX polypeptide comprising an amino acid sequence that has at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% identity to SEQ ID NO: 1;

(ix) is immobilized to a solid support, particle, or matrix;

(x) catalyzes the oxidation of glucuronic acid to glucaric acid at alkaline pH, such as from 7.5 to 11, 8 to 11, 8.5 to 11, 9 to 11, 9.5 to 11, or 9.5 to 10.5;

(xi) catalyzes the oxidation of glucuronic acid to glucaric acid at a temperature above 37° C., such as between 38° C. and 45° C., 38° C. and 44° C., 38° C. and 43° C., 38° C. and 42° C., 39° C. to 41° C., or about 40° C.;

(xii) catalyzes the oxidation of glucuronic acid to glucaric acid in the absence of exogenous cofactor supplementation, such as NAD; or (xiii) any combination of (i) to (xii).

7. The process of any one of items 1 to 6, wherein the enzymatic conversion of the glucuronic acid to glucaric acid occurs:

(i) in a buffer having an ionic strength of at least 100, 150, 200, 250, 300, 350, 400, 450, or 500 mM, wherein said ionic strength increases the molar ratio of glucaric acid to glucuronic acid produced by said process, as compared to a buffer having an ionic strength less than 100 mM or less than 50 mM;

(ii) in a buffer having an alkaline pH, such as from 7.5 to 11, 8 to 11, 8.5 to 11, 9 to 11, 9.5 to 11, or 9.5 to 10.5;

(iii) at a temperature above 37° C., such as between 38° C. and 45° C., 38° C. and 44° C., 38° C. and 43° C., 38° C. and 42° C., 39° C. to 41° C., or about 40° C.;

(iv) in the absence of exogenous cofactor supplementation, such as NAD supplementation; or (v) any combination of (i) to (iv).

8. The process of any one of items 1 to 7, wherein the glucuronic acid is obtained from enzymatic treatment of a glucuronic acid-substituted polysaccharide, such as glucuronic acid-substituted xylan, glucuronic acid-substituted arabinoxylan, and/or glucuronic acid-substituted ulvan, glucuronoxylans from hardwood (deciduous) trees, arabinoglucuronoxylans from softwood (coniferous) trees, glucuronoarabinoxylan from agricultural fibre, or ulvan from green algae.

9. The process of item 8, wherein the glucuronic acid is obtained from enzymatic treatment of the glucuronic acid-substituted polysaccharide with a glycoside hydrolase.

10. The process of item 9, wherein the glycoside hydrolase:

(i) is a glucuronidase catalyzing the release of glucuronic acid from glucuronic acid-substituted polysaccharide (e.g., glucuronoxylan);

(ii) is a glucuronidase belonging to the glycoside hydrolase (GH) family GH2, GH67, or GH115;

(iii) is a glucuronidase (e.g., alpha-glucuronidase and/or beta-glucuronidase);

(iv) is AxyAgu115A or SdeAgu115A, or a variant thereof that catalyzes the release of glucuronic acid from glucuronoxylan;

(v) is a AxyAgu115A or SdeAgu115A variant comprising an amino acid sequence that has at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% identity to SEQ ID NO: 4 or 5; or (vi) any combination of (i) to (v).

11. The process of any one of items 8 to 10, wherein the enzymatic treatment of the glucuronic acid-substituted polysaccharide to release the glucuronic acid and the conversion of glucuronic acid to glucaric acid by the oxidase or oxidoreductase are performed in the same reaction vessel, preferably at alkaline pH (such as from 7.5 to 11, 8 to 11, 8.5 to 11, 9 to 11, 9.5 to 11, or 9.5 to 10.5).

12. The process of any one of items 8 to 11, which is a sequential two-step process comprising the enzymatic treatment of the glucuronic acid-substituted polysaccharide to release the glucuronic acid, followed by the conversion of glucuronic acid to glucaric acid by the oxidase or oxidoreductase.

13. The process of any one of items 9 to 12, wherein the glycoside hydrolase and/or the oxidase or oxidoreductase are immobilized to a solid support, particle, or matrix.

14. The process of any one of items 1 to 13, wherein the glucuronic acid:

(i) is or comprises substituted glucuronic acid (e.g., methyl glucuronic acid or, more specifically, 4-O-methyl glucuronic acid), which is enzymatically converted to the corresponding substituted glucaric acid by said recombinant oxidase or oxidoreductase;

(ii) is substantially enantiomerically pure substituted D-glucuronic acid (e.g., methyl D-glucuronic acid or, more specifically, 4-O-methyl D-glucuronic acid), which is enzymatically converted to the corresponding substantially enantiomerically pure substituted D-glucaric acid by said recombinant oxidase or oxidoreductase; or (iii) both (i) and (ii).

15. The process of any one of items 8 to 14, further comprising the use of a catalase to catalyze the breakdown hydrogen peroxide generated by the oxidase or oxidoreductase.

16. The process of any one of items 8 to 15, wherein the glucuronic acid-stripped polysaccharide produced the enzymatic treatment of the glucuronic acid-substituted polysaccharide is isolated or purified from the released glucuronic acid or glucaric acid.

17. A process for producing glucaric acid from a feed-stock, the process comprising:
 (a) providing a feedstock comprising a glucuronic acid-substituted polysaccharide;
 (b) enzymatically hydrolyzing the glucuronic acid-substituted polysaccharide to produce glucuronic acid and glucuronic acid-stripped polysaccharide;
 (c) enzymatically oxidizing the glucuronic acid to glucaric acid; and
 (d) separating or isolating the glucaric acid from the glucuronic acid-stripped polysaccharide.

18. The process of item 17, wherein step (b) is as defined in any one of items 1 to 7; and/or step (c) is as defined in any one of items 8 to 11.

19. The process of item 17 or 18, which is a process as defined in any one of items 12 to 16.

20. A composition comprising substantially enantiomeri-cally pure unsubstituted D-glucaric acid, substituted D-glucaric acid, methyl D-glucaric acid, or 4-O-methyl D-glucaric acid.

21. The composition of item 20, which is produced by the process of any one of items 1 to 19.

22. The composition of item 20 or 21, wherein the unsubstituted D-glucaric acid, substituted D-glucaric acid, methyl D-glucaric acid, or 4-O-methyl D-glucaric acid is comprised as a substantially single acid form.

23. The composition of any one of items 20 to 22 for use in the production of nylon.

24. A composition comprising the oxidase or oxi-doreductase as defined in any one of items 1 to 7 or 13, and further comprising: (a) the glucuronic acid as defined in item 8, 9, or 14; (b) the glycoside hydrolase as defined in item 10 or 13; (c) the catalase as defined in item 15; (d) the unsubstituted or substituted glucaric acid as defined in item 20 or 22; or (e) any combination of (a) to (d).

25. A recombinant oxidase or oxidoreductase for use in catalyzing the conversion of substituted or unsubsti-tuted glucuronic acid to substituted or unsubstituted glucaric acid, the recombinant oxidase or oxi-doreductase being the oxidase or oxidoreductase as defined in any one of items 1 to 7 or 13.

26. The recombinant oxidase or oxidoreductase for use of item 25, which is for use in the process of any one of items 1 to 19.

EXAMPLES

Example 1: Materials and Methods 1.1 Materials

4-O-methyl glucuronoxylan from beechwood, also known as glucuronoxylan (cat. no. M5144) was purchased from Sigma (USA). 4-O-methyl D-glucuronic acid (MeGlcA, purity >95%, by 1H-NMR, cat. no. MG244) was purchased from Synthose Inc. (Canada) while D-glucuronic acid (GlcA, not methylated, purify >98% by GC, cat. no. G5269) was purchased from Sigma (USA). Catalase (cat. no. C40, ≥10,000 units/mg protein) and glucose oxidase (cat. no. G2133) were purchased from Sigma (USA). Two Thermobifida *fusca* bacterial xylanases, Xyn10B and Xyn11A used were originally published in Irwin et al., 1994 and Kim et al., 2004, respectively, while a fungal xylanase (cat. no. NS51024) was obtained from Novozymes (Den-mark).

1.2 Protein Production

AxyAgu115A and GOOX-Y300A were produced based on the previous publications (Vuong et al., 2013; Yan et al., 2017). Briefly, for AxyAgu115A purification, *Escherichia coli* BL21 (λDE3) CodonPlus™ was grown at 37° C. in Luria-Bertani medium containing 500 mM sorbitol, 2.5 mM glycine betaine, 34 µg/mL chloramphenicol and 100 µg/mL ampicillin. Cells were induced by 0.5 mM IPTG at 15° C. for 16 h. Cells were then sonicated in a binding buffer (300 mM NaCl, 50 mM HEPES pH 7.0, 5% glycerol, and 5 mM imidazole). After centrifugation, the supernatant was incu-bated with Ni-NTA resin for 2 h at 4° C., and the protein was eluted with an elution buffer (300 mM NaCl, 50 mM HEPES pH 7.0, 5% v/v glycerol, and 250 mM imidazole). The protein was purified further using a Bio-Gel P10 column. Other GOOX variants were produced in the previous work (Foumani et al., 2011; Vuong and Master, 2014; Vuong et al., 2013). The concentration and purity of these recombi-nant proteins were determined by gel densitometry using a bovine serum albumin (Thermo Fisher Scientific, USA) as the standard. All recombinant GOOX enzymes were pro-duced and characterized herein correspond to wild-type GOOX sequence of SEQ ID NO: 1, and further comprise at the C-terminus a myc-tag followed by 6xHis-tag for detec-tion and purification purposes.

1.3 Enzymatic Hydrolysis and Oxidation

Glucuronoxylan (6%) was incubated with AxyAgu115A (10 µg/mL) and GOOX-Y300A (10 µg/mL) in 100 mM Tris buffer pH 8.0 at 40° C. in a rotator oven for up to 72 h. The reactions were then vacuum-filtered using 96-well filter plates (0.22-µm PVDF membrane) (Millipore, USA) in a Tecan liquid handler (500 mbar) (Tecan Trading AG, Swit-zerland). Enzymatic products in the flow-through were con-firmed by mass spectrometry and quantified by HPAEC-PAD analysis.

The specific activity of GOOX-Y300A (16 nM) on MeGlcA and GlcA (1 mM) was measured in 50 mM Tris buffer pH 8.0 at 40° C. The amount of methyl glucaric acid was determined by measuring the release of $H_2O_2$ using a previously published colorimetric assay (Lin et al., 1991). The kinetics of GOOX-Y300A on these acidic sugars were measured at the same condition, but using up to 60 mM MeGlcA and GlcA and in 0.3 M Tris buffer pH 8.0.

Untreated glucuronoxylan (2%) and those were pre-treated with AxyAgu115A (10 µg/mL) alone or with both AxyAgu115A and GOOX-Y300A (10 µg/mL each) were individually incubated with bacterium xylanases Xyn10B and Xyn11A (0.1 µM) in 50 mM potassium phosphate pH 6.0 for 16 h at 40° C. in a rotator (6 rpm). These xylan samples were also incubated in MilliQ™ water with Novozymes fungal xylanase NS51024 ($8\times10^{-4}$%, w/v) for 20 min at 40° C. at 700 rpm in a thermomixer (Eppendorf, USA). The release of xylose and xylo-oligosaccharides was quantified by HPAEC-PAD analysis after vacuum filtration.

1.4 Quantification of MeGlcA from
Glucuronoxylan

MeGlcA present in glucuronoxylan was released by a modified acidic methanolysis (De Ruiter et al., 1992). Glucuronoxylan (10 mg), as well as MeGlcA (1 mM), was treated with 1 mL of 2 M HCl in anhydrous methanol in glass vials at 100° C. for 3 h. Samples were then dried by nitrogen flow, and re-dissolved in MilliQ™ water for HPAEC-PAD analysis.

1.5 $H_2O_2$ Inhibition Assay

AxyAgu115A (10 µg/mL) was incubated with 1% glucuronoxylan in 50 mM Tris buffer pH 8.0 in the presence of various $H_2O_2$ concentrations (0.01-100 mM). MeGlcA (1 mM) was also incubated with the same $H_2O_2$ concentrations. The reactions were kept in the dark at 40° C. for 16 h in a thermomixer (Eppendorf, USA). Catalase (200 µg/mL) was then added, and the reactions were kept incubating for another 30 min to remove $H_2O_2$ before HPAEC-PAD analysis.

1.6 Anion-Exchange Chromatography

Anion-exchange chromatography was performed using Dowex 1×8 anion exchange resin (50-100 mesh) in a glass column (2.6 cm ID×30 cm) connected to a BioLogic Duo-Flow FPLC unit with a Quadtec UV detector (Bio-Rad, USA) with flow rates ranging from 1-3.0 mL/min MilliQ™ water was used as the primary eluent, and acidic sugars were eluted using a 0-2 M ammonium acetate (pH 6.5) gradient. Fractions containing eluted products were desalted and concentrated by lyophilization. The presence of sugar products in fractions was detected by spotting the samples on silica plates on aluminum backing (Sigma-Aldrich, USA), a mobile phase consisting of ethyl acetate/acetic acid/isopropanol/formic acid/water (25:10:5:1:15) was used. Carbohydrates were visualized using the diphenylamineaniline stain (MacCormick et al., 2018).

1.7 HPAEC-PAD Analysis

Reaction samples were vacuum-filtered using 0.22-µm, PVDF filter plates (Millipore, USA) with a Tecan liquid handler (500 mbar) (Tecan Trading AG, Switzerland). The flow-through was collected to Nunc™ 96-well polypropylene microplates (Thermo Fisher Scientific, USA), and covered with Nunc™ 96-well silicone cap mats. The presence of acidic sugars was detected using an ICS5000 HPAEC-PAD system (Dionex, USA) with a CarboPac PA1 (2×250 mm) analytical column (Dionex, USA). The HPAEC-PAD samples were eluted at 0.25 mL/min using NaOAc gradient (0-0.5 M) in 0.1 M NaOH. Chromatograms were analyzed using Chromeleon 7.2 (Dionex, USA).

1.8 Nanospray Ionization Ion-Trap Mass Spectrometry (NSI-MS)

Reaction solutions were prepared in 50% methanol and directly injected using a nano-ESI source on a Q-Exactive mass spectrometer (Thermo Scientific, USA) with a disposable pico-emitter. Samples were analyzed in a negative mode at a spray voltage of 2.5 kV, capillary temperature of 250° C., automatic gain control target of $1×10^6$, injection time of 100 ms, and resolution of 140,000. Spectra were analyzed using Qual Browser in Thermo Xcalibur (v2.2) software (Thermo Scientific, USA).

1.8 LC-MS Analysis

Reaction solutions were vacuum-filtered using 0.22-µm, PVDF filter plates (Millipore, USA) and collected into 96-well, skirted PCR plates (Eppendorf, USA) covered with adhesive aluminum sealer (Greiner Bio-One GmbH, Austria). Each sample was then analyzed using a Q-Exactive mass spectrometer (Thermo Scientific, USA), equipped with an Ultimate 3000 HPLC system (Thermo Scientific, USA) and a Hypersil GOLD column (50×2.1 mm) (Thermo Scientific, USA).

Example 2: Release of 4-O-methyl D-glucuronic Acid by AxyAgu115A

Figure 2:
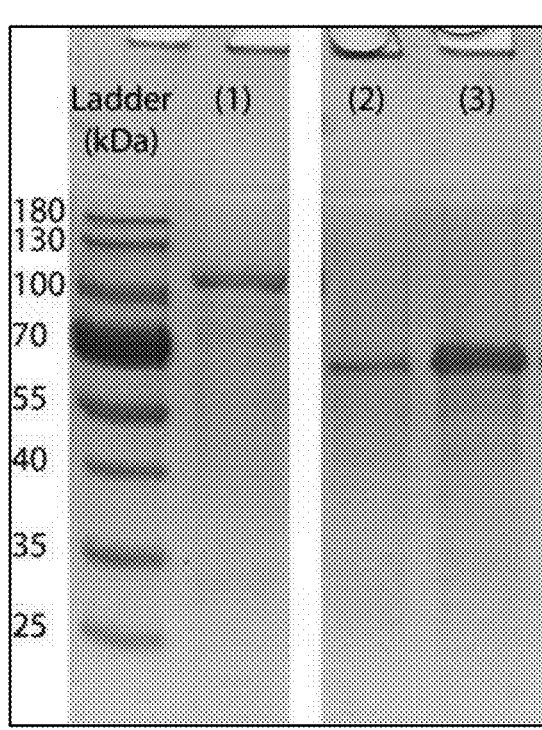
FIG. 2: SDS-PAGE of purified AxyAgu115A and GOOX-Y300A. Lane 1: Purified AxyAgu115A (the theoretical molecular mass=110 kDa); lanes 2 and 3: Different amount of purified GOOX-Y300A (the theoretical molecular mass=56 kDa including a FAD cofactor).

AxyAgu115A was produced with high purity (FIG. 2). The treatment of glucuronoxylan with AxyAgu115A released only MeGlcA, as analyzed by HPAEC-PAD (FIG. 3), and no additional release of MeGlcA was seen after 16 h. The half-life of AxyAgu115A at 40° C. was 24 h (Yan et al., 2017), thus the enzyme remained active during 16-h hydrolysis. The release of MeGlcA was also confirmed by NSI-MS. A mass scan from 100 m/z to 1,000 m/z showed that MeGlcA and its dimer are the two major peaks in the spectrum (FIG. 4). The simulated spectrum of MeGlcA was also matched well to the acquired spectrum.

The concentration of MeGlcA released from 1.5 g glucuronoxylan was 21.6±1.2 mM, calculated by on the MeGlcA standard curve (FIG. 5) whereas the estimated molar concentration of MeGlcA, based on a previous analysis of glucuronoxylan composition (Teleman et al., 2002), was 24.4 mM. Therefore, AxyAgu115A was able to release almost all of MeGlcA present in glucuronoxylan. This finding was supported by methanolysis, where the total concentration of MeGlcA released from glucuronoxylan was measured at approximately 15.6 mM. The lower concentration of MeGlcA by methanolysis is due to partial MeGlcA degradation by a high temperature (100° C.) and acid concentration (2M HCl), as nearly 20% of MeGlcA was lost during methanolysis. A similar percentage of MeGlcA degradation by methanolysis was also previously reported (Bertaud et al., 2002).

Figure 6A:
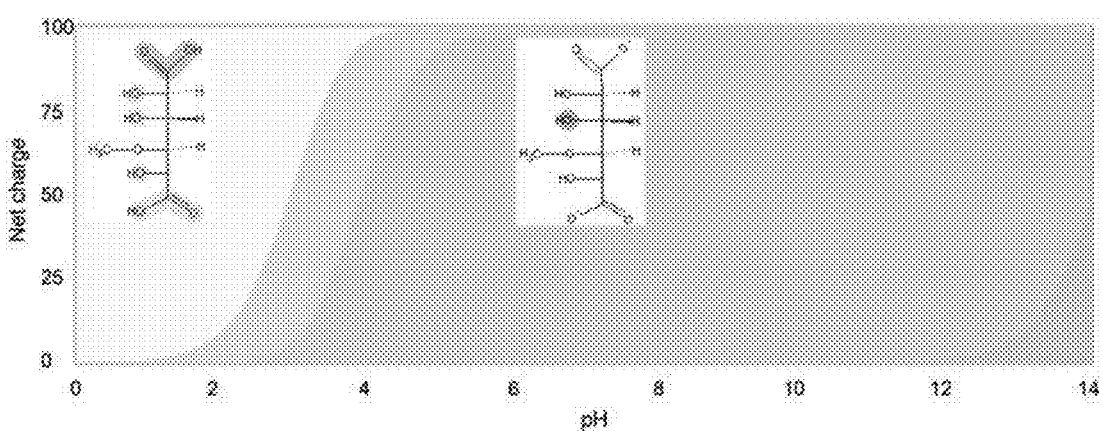
FIG. 6A: Net charge of MeGlcA at different pH values, as predicted by ACD/Labs 2.0 v5.
Figure 6B:
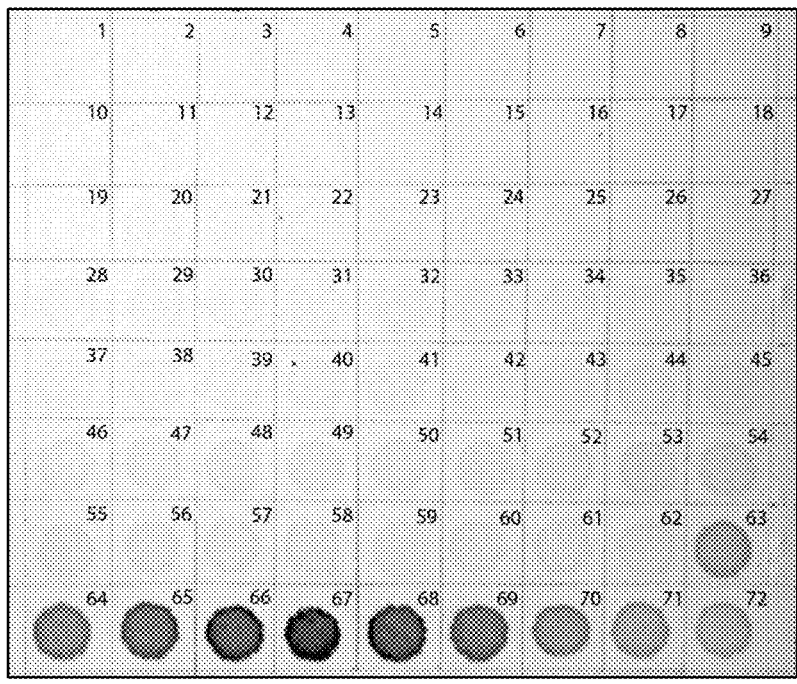
FIG. 6B: Colorimetric analysis of anion-exchange fractions from AxyAgu115A digestion of glucuronoxylan. Each fraction (4 μL) was loaded on one square, numbered from 1 to 72, and the silica plate was stained with diphenylamineaniline to detect the presence of MeGlcA, which initiated to show up in the eluent with higher than 0.5 M ammonium acetate (from fraction 63).

The pKa of MeGlcA is 3.0, as predicted by ACD/Labs 2.0 v5 (www.ilab.acdlabs.com) (FIG. 6A), so at alkaline conditions, MeGlcA is negatively charged. Therefore, anion exchange chromatography was used to purify MeGlcA released by AxyAgu115A, which showed that the acidic sugar was eluted from Dowex resin when the concentration of ammonium acetate was higher than 0.5 M (FIG. 6B) Ammonium acetate was then removed by freeze-drying.

Example 3: Oxidation of 4-O-methyl D-glucuronic Acid by GOOX Variants

Figure 11:
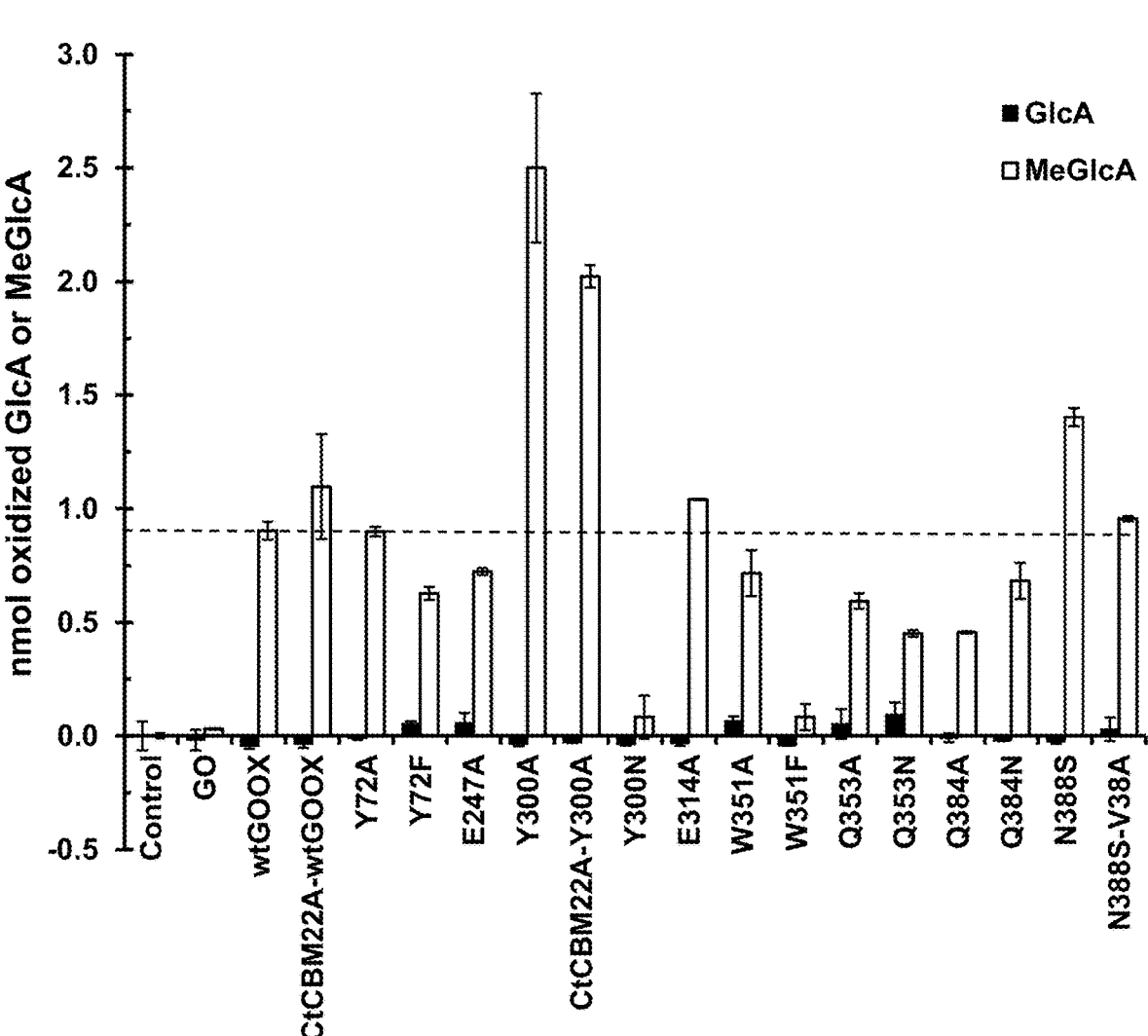
FIG. 11: Activity screening of GOOX variants and glucose oxidase (GO) on GlcA and MeGlcA substrates. The enzymes (16 nM) were assayed at 37° C. with 10 mM GlcA and 1 mM MeGlcA in 100 mM Tris buffer pH 8.0 (for GOOX variants) or 50 mM sodium acetate pH 5.0 (for GO). The dotted line indicates the activity of GOOX-VN for MeGlcA for ease of comparison. "CtCBM22A-wtGOOX" and "CtCBM22A-Y300A" represent fusion proteins where the C terminus of the xylan-binding protein CtCBM22A (described in Vuong and Master, 2014) is fused to the N terminus GOOX.

A preliminary screening of 17 GOOX variants on 100 mM GlcA and 10 mM MeGlcA strikingly revealed that the methylated form of D-glucuronic acid was the preferred substrate (FIG. 11 and Table below).

|  | nmol oxidized GlcA | | nmol oxidized MeGlcA | |
|---|---|---|---|---|
|  | Mean | Stand. dev. | Mean | Stand. dev. |
| Control | 0 | 0.06337 | 0 | 0.0116 |
| GO | −0.01829 | 0.04526 | 0.03046 | 0.00166 |
| wtGOOX | −0.04572 | 0.01164 | 0.90323 | 0.03976 |
| CtCBM22A-wtGOOX | −0.03658 | 0.01681 | 1.09653 | 0.23029 |
| Y72A | −0.01097 | 0.00647 | 0.89972 | 0.02154 |
| Y72F | 0.05395 | 0.01035 | 0.62793 | 0.02816 |
| E247A | 0.05669 | 0.04267 | 0.72399 | 0.01491 |

-continued

| | nmol oxidized GlcA | | nmol oxidized MeGlcA | |
|---|---|---|---|---|
| | Mean | Stand. dev. | Mean | Stand. dev. |
| Y300A | −0.03566 | 0.01035 | 2.5 | 0.32851 |
| CtCBM22A-Y300A | −0.02926 | 0.00129 | 2.0232 | 0.0497 |
| Y300N | −0.03749 | 0.00517 | 0.08201 | 0.09444 |
| E314A | −0.03292 | 0.01164 | 1.0403 | 0.00166 |
| W351A | 0.06492 | 0.02069 | 0.71657 | 0.10079 |
| W351F | −0.04298 | 0 | 0.08201 | 0.05799 |
| Q353A | 0.05212 | 0.06466 | 0.59396 | 0.03314 |
| Q353N | 0.09327 | 0.05302 | 0.4522 | 0.01491 |
| Q384A | −0.00914 | 0.0194 | 0.45689 | 0.00497 |
| Q384N | −0.02195 | 0.00129 | 0.68299 | 0.07952 |
| N388S | −0.02652 | 0.00776 | 1.4023 | 0.03976 |
| N388S-V38A | 0.02835 | 0.05173 | 0.95595 | 0.0116 |

Figure 7:
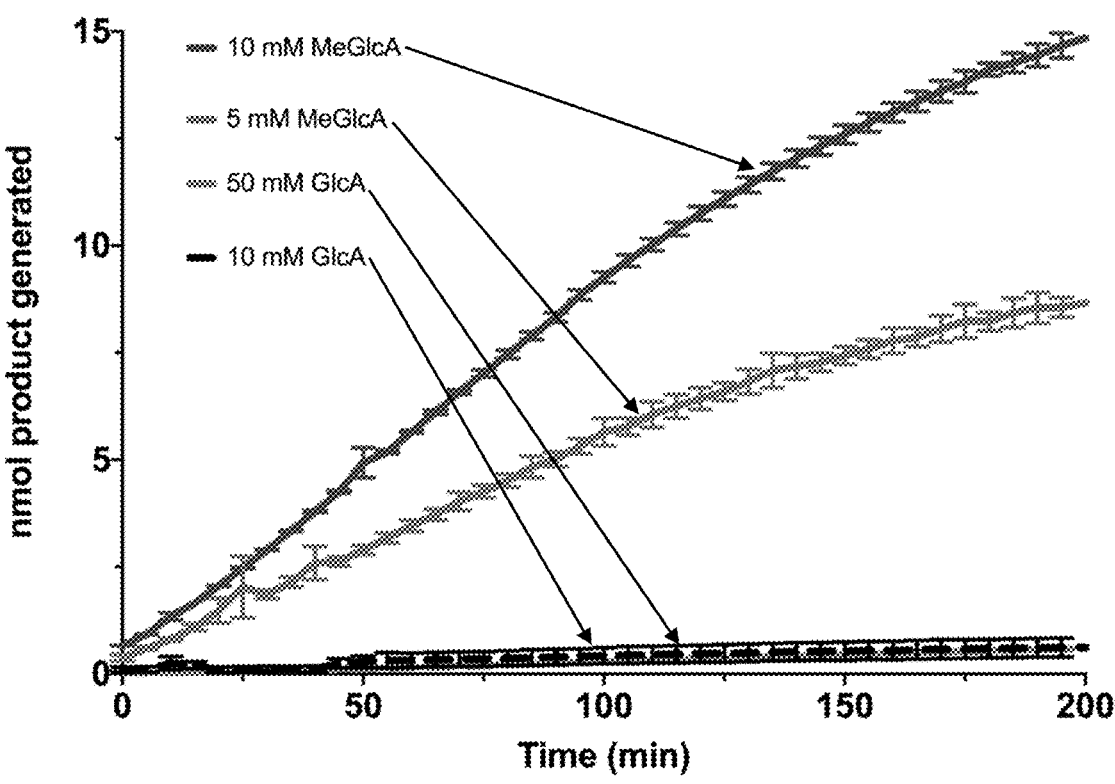
FIG. 7: Substrate preference of GOOX-Y300A on GlcA (10 and 50 mM) and MeGlcA (5 and 10 mM).

A commercial glucose oxidase (GO, cat. no. G2133 from Sigma) did not show any activity on GlcA and MeGlcA. Wild-type GOOX (wtGOOX) and all GOOX variants shown in FIG. 11 and in the Table above exhibited substrate preference for MeGlcA over GlcA. GOOX variants 300A and 388S exhibited improved activity over wtGOOX with MeGlcA as substrate, and GOOX variants 72F, 247A, 351A, 353A or 353N, and 388S exhibited improved activity over wtGOOX with GlcA as substrate. The GOOX variant Y300A showed the highest specific activity on MeGlcA (FIG. 7). Therefore, this GOOX variant, hereafter GOOX-Y300A, was produced and used for further characterization (FIG. 2).

Figure 8:
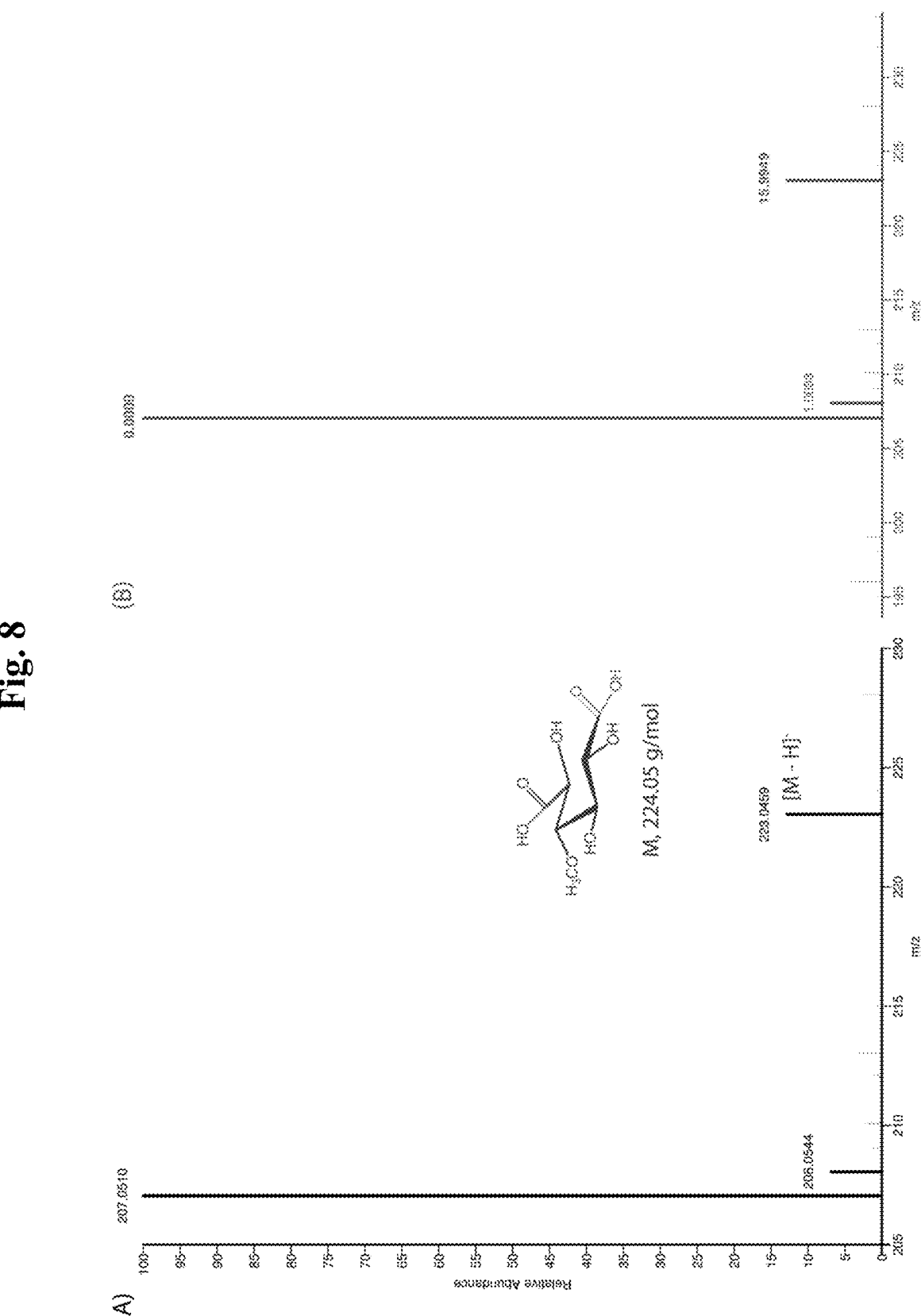
FIG. 8: NSI-MS spectra of MeGlcA oxidation. (A) Mass spectrum of GOOX-Y300A activity on 1 mM MeGlcA, (B) The corrected mass spectrum to confirm the addition of one oxygen (15.9949 m/z).

The formation of methyl glucaric acid by GOOX-Y300A was confirmed by NSI-MS (FIG. 8), where methyl glucaric acid was seen at 223.05 m/z, confirming oxidation (addition of 15.99 m/z) of MeGlcA. There was a dose response for the production of methyl glucaric acid, as the relative abundance of methyl glucaric acid increased when the substrate concentration was raised from 1 mM to 10 mM. Consistent with this prediction, kinetic analysis of GOOX-Y300A on MeGlcA revealed a $K_m$ of 21±2 mM and $k_{cat}$ of 0.91±0.06 $min^{-1}$ This $K_m$ value is higher than that of GOOX-Y300A on glucose (8.1 mM) while its $k_{cat}$ was nearly three orders of magnitude lower (Foumani et al., 2011), suggesting the necessary of future rational engineering of GOOX-Y300A for improvement of MeGlcA catalysis.

In an attempt to improve the oxidation of GOOX-Y300A, the ionic strength of the Tris buffer was increased to 300 mM and the concentration of MeGlcA was brought up to 60 mM, higher than its $K_m$. NSI-MS confirmed an increase in the intensity ratio of methyl glucaric acid over MeGlcA (FIG. 9). Furthermore, based on substrate consumption, HPAEC-PAD analyses showed that the efficiency of GOOX-Y300A on MeGlcA oxidation after 24 h was 62%, which is 55% higher than the non-selective oxidation of glucose to produce glucaric acid (Armstrong et al., 2017). Provided that a similar xylan source was used, the conversion yield reported from the 3-enzyme pathway by Lee et al. (2016) (Lee et al., 2016a) was estimated ca. 20%, as determined by measuring NADH absorbance at 340 nm.

Methyl glucaric acid was also chemically produced from MeGlcA using $Ca(OH)_2$ and NaOH; however, the highest yield was only 24%, and the final reaction solution contained eight other dicarboxylic acids (Löwendahl et al., 1975). Several approaches that use heterogeneous metal catalysts including Pt/C, Pt/Au, Au/C or AuBi/C or $Pt_1Cu_3/TiO_2$ (Lee et al., 2016b; Solmi et al., 2017) could gain a complete conversion of glucose; however, the full selectivity of glucose to GlcAA is not achievable, requiring a separation of GlcAA from other oxidized products, including those from overoxidation and C—C breaking. This low selectivity would prevent those chemo-catalytic approaches from oxidation of complex feedstock such carbohydrate-rich hydrolysate of hemicellulose generated in pulp paper or corn-based ethanol industries.

When GOOX-Y300A oxides MeGlcA, it also reduces molecular oxygen to hydrogen peroxide; therefore, to test for potential degradation of MeGlcA by $H_2O_2$, MeGlcA was incubated with different concentrations of $H_2O_2$ in 50 mM Tris pH 8.0, no loss of MeGlcA was seen even by HPAEC-PAD at 100 mM $H_2O_2$ (FIG. 10), which is nearly five times higher than $K_m$ of GOOX-Y300A on MeGlcA. Even at 200 mM $H_2O_2$, GOOX-Y300A retained more than 50% of its activity on glucose and 100% of its activity on cellobiose (Vuong et al., 2016). Furthermore, $H_2O_2$ is less stable in alkaline conditions, when exposed to light, and particularly at elevated temperatures (40° C.) (Yazici and Deveci, 2010). This suggests the addition of catalase is not necessary.

Example 4: Sequential One-Pot Reaction for Methyl Glucaric Acid Production

Figure 10A:
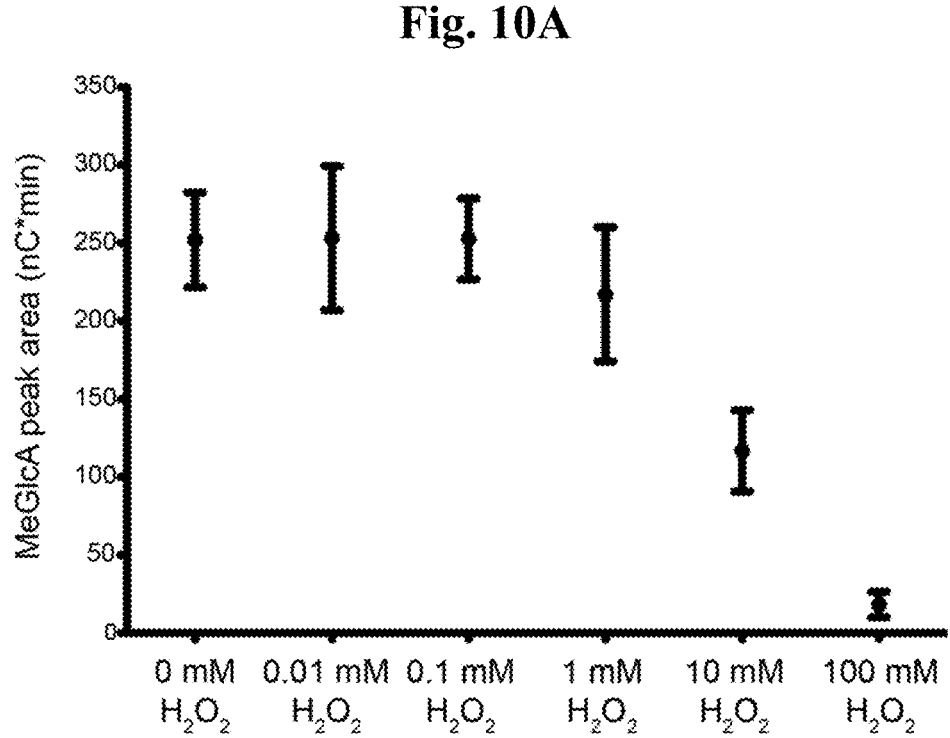
FIG. 10: HPAEC-PAD analyses of $H_2O_2$ effects on AxyAgu115A activity and MeGlcA degradation. (A) Higher concentrations of $H_2O_2$ lowered the amount of MeGlcA released (as quantified by peak area) from glucuronoxylan by AxyAgu115A. (B) The presence of $H_2O_2$ did not cause a loss of MeGlcA (0.7 mM).
Figure 10B:
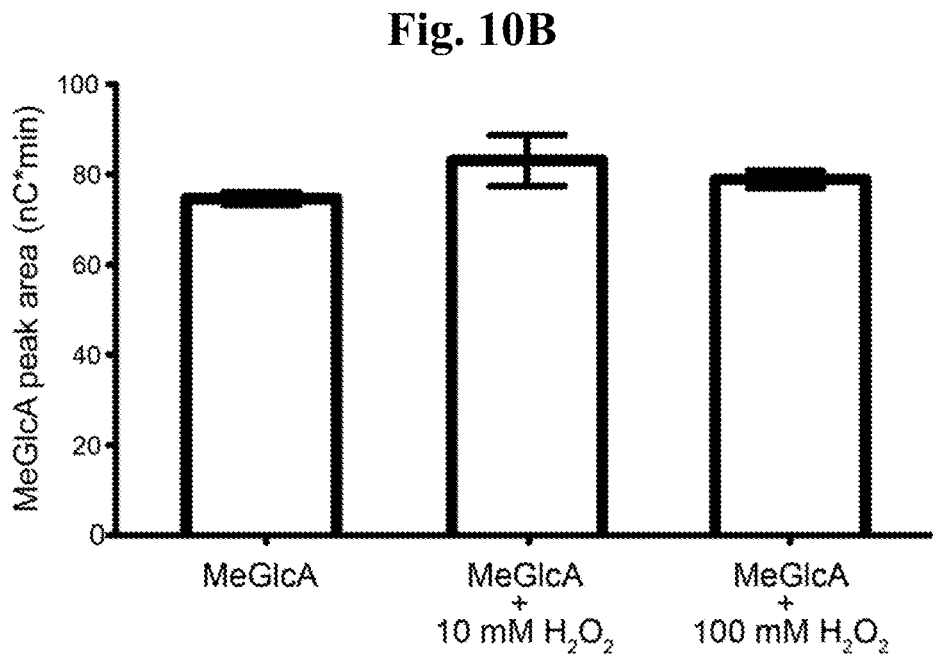

The MeGlcA concentration released by AxyAgu115A from 6% glucuronoxylan after 16 h was around the $K_m$ of GOOX-Y300A on this acidic sugar, supporting the usage of GOOX-Y300A and AxyAgu115 in a one-pot reaction. Furthermore, both enzymes prefer alkaline conditions, which offer several advantages, including the ability to increase xylan loading (e.g., to 6% w/v used here, compared to 1% reported in Lee et al. (2016) (Lee et al., 2016a), and to reduce the presence of lactone forms of glucaric acid (Hong et al., 2016) that could hinder product recovery. However, AxyAgu115A activity was inhibited when the concentration of $H_2O_2$ was greater than 1 mM, and approximately half of AxyAgu115A activity was lost in the presence of 10 mM $H_2O_2$ (FIG. 10). Therefore, GOOX-Y300A subsequently added after AxyAgu115A digestion may be advantageous. HPAEC-PAD analysis indicated that most of MeGlcA was released by AxyAgu115A during 4 h of incubation. Thus, a one-pot sequential reaction was performed where GOOX-Y300A was added to the reaction after pre-hydrolysis of glucuronoxylan by AxyAgu115A for 4 h. Following 16 h of incubation with GOOX-Y300A, methyl glucaric acid yields were similar to those achieved using the two-pot sequential system described above (i.e., 60% yield as confirmed by LC-MS).

Example 5: Simplified Separation of Stripped Xylan

The xylan after AxyAgu115A and GOOX-Y300A treatments formed a hydrogel-like material (FIG. 12), which was easily separated from the reaction by a quick centrifuge (10,000×g for 1 min). After washing with Mil water to remove any remaining soluble products, the resulting xylan was still hydrolysable by both bacterial xylanases Xyn10B and Xyn11A (FIG. 13), and by Novozymes fungal xylanase NS51024.

REFERENCES

Armstrong R D, Kariuki B M, Knight D W, Hutchings G J. How to synthesise high purity, crystalline D-glucaric acid selectively. European J Org Chem. 2017; 2017:6811-4.

Bertaud F. Evaluation of acid methanolysis for analysis of wood hemicelluloses and pectins. Carbohydrate Polymers. 2002; 48:319-24.

Bozell J J, Petersen G R. Technology development for the production of biobased products from biorefinery carbohydrates—the US Department of Energy's "Top 10" revisited. Green Chemistry. 2010; 12:539.

Chen N, Wang J Y, Zhao Y Y, Deng Y. Metabolic engineering of Saccharomyces cerevisiae for efficient production of glucaric acid at high titer. Microbial Cell Factories. 2018; 17:67.

De Ruiter G A, Schols H A, Voragen A G J, Rombouts F M. Carbohydrate analysis of water-soluble uronic acid-containing polysaccharides with high-performance anion-exchange chromatography using methanolysis combined with TFA hydrolysis is superior to four other methods. Anal Biochem. 1992; 207:176-85.

Foumani M, Vuong T V, Master E R. Altered substrate specificity of the gluco-oligosaccharide oxidase from Acremonium strictum. Biotechnol Bioeng. 2011; 108: 2261-9.

Hong C H, Kim S H, Kim Y G, Shin N R. Method for producing glucaric acid. U59227904 B1: Hyundai Motor Company, Snu R&db Foundation; 2016.

Irwin D, Jung E D, Wilson D B. Characterization and sequence of a Thermomonospora fusca xylanase. Appl Environ Microbiol. 1994; 60:763-70.

Kim J H, Irwin D, Wilson D B. Purification and characterization of Thermobifida fusca xylanase 10B. Can J Microbiol. 2004; 50:835-43.

Lee C C, Kibblewhite R E, Paavola C D, Orts W J, Wagschal K. Production of glucaric acid from hemicellulose substrate by rosettasome enzyme assemblies. Mol Biotechnol. 2016a; 58:489-96.

Lee J, Saha B, Vlachos D G. Pt catalysts for efficient aerobic oxidation of glucose to glucaric acid in water. Green Chemistry. 2016b; 18:3815-22.

Lin S-F, Yang T-Y, Inukai T, Yamasaki M, Tsai Y-C. Purification and characterization of a novel glucooligosaccharide oxidase from Acremonium strictum T1. Biochim Biophys Acta. 1991; 1118:41-7.

Liu Y, Gong X, Wang C, Du G, Chen J, Kang Z. Production of glucaric acid from myo-inositol in engineered Pichia pastoris. Enzyme Microb Technol. 2016; 91:8-16.

Lowendahl L, Petersson G, Samuelson O. Formation of dicarboxylic acids from 4-O-methyl-D-glucuronic acid in alkaline solution in the presence and absence of oxygen. Carbohydrate Research. 1975; 43:355-9.

MacCormick B, Vuong T V, Master E R. Chemo-enzymatic synthesis of clickable xylo-oligosaccharide monomers from hardwood 4-O-methylglucuronoxylan. Biomacromolecules. 2018; 19:521-30.

Moon T S, Yoon S H, Lanza A M, Roy-Mayhew J D, Prather K L. Production of glucaric acid from a synthetic pathway in recombinant Escherichia coli. Appl Environ Microbiol. 2009; 75:589-95.

Rorrer N A, Dorgan J R, Vardon D R, Martinez C R, Yang Y, Beckham G T. Renewable unsaturated polyesters from muconic acid. ACS Sustainable Chemistry & Engineering. 2016; 4:6867-76.

Solmi S, Morreale C, Ospitali F, Agnoli S, Cavani F. The oxidation of D-glucose to glucaric acid using Au/C catalysts. ChemCatChem. 2017:DOI:10.1002/cctc.201700089.

Teleman A, Tenkanen M, Jacobs A, Dahlman O. Characterization of O-acetyl-(4-O-methylglucurono)xylan isolated from birch and beech. Carbohydr Res. 2002; 337:373-7.

Vuong T V, Foumani M, MacCormick B, Kwan R, Master E R. Direct comparison of gluco-oligosaccharide oxidase variants and glucose oxidase: substrate range and $H_2O_2$ stability. Sci Rep. 2016; 6:37356.

Vuong T V, Master E R. Fusion of a xylan-binding module to gluco-oligosaccharide oxidase increases activity and promotes stable immobilization. PLOS One. 2014; 9:e95170.

Vuong T V, Vesterinen A H, Foumani M, Juvonen M, Seppala J, Tenkanen M, et al. Xylo- and cello-oligosaccharide oxidation by gluco-oligosaccharide oxidase from Sarocladium strictum and variants with reduced substrate inhibition. Biotechnol Biofuels. 2013; 6:148.

Wang W, Yan R, Nocek B P, Vuong T V, Di Leo R, Xu X, Cui H, Gatenholm P, Toriz G, Tenkanen M, Savchenko A, Master E R. Biochemical and structural characterization of a five-domain GH115 α-glucuronidase from the marine bacterium Saccharophagus degradans 2-40T. J Biol Chem. 2016; 291(27):14120-33.

Yan R, Vuong T V, Wang W, Master E R. Action of a GH115 alpha-glucuronidase from Amphibacillus xylanus at alkaline condition promotes release of 4-O-methylglucopyranosyluronic acid from glucuronoxylan and arabinoglucuronoxylan. Enzyme Microb Technol. 2017; 104:22-8.

Yazici E Y, Deveci H. Factors affecting decomposition of hydrogen peroxide. Proceedings of the XIIth International Mineral Processing Symposium 2010. p. 609-16.

The invention claimed is:

1. A process for producing 4-O-methyl glucaric acid, comprising:

providing a solution comprising dissolved 4-O-methyl glucuronic acid;

providing a recombinant gluco-oligosaccharide oxidase (GOOX) having at least 99% sequence identity to SEQ ID NO: 1; and contacting the dissolved 4-O-methyl glucuronic acid with said recombinant GOOX under conditions that catalyze enzymatic conversion of the 4-O-methyl glucuronic acid to 4-O-methyl glucaric acid.

2. The process of claim 1, wherein the recombinant GOOX comprises 300A, 314A, or 388S, relative to the amino acid positioning of SEQ ID NO: 1.

3. The process of claim 1, wherein the recombinant GOOX is immobilized to a solid support, particle, or matrix.

4. The process of claim 1, wherein the enzymatic conversion of the 4-O-methyl glucuronic acid to the 4-O-methyl glucaric acid by the recombinant GOOX is performed at a pH of 7.5 to 11.

5. The process of claim 1, wherein the enzymatic conversion of the 4-O-methyl glucuronic acid to the 4-O-methyl glucaric acid by the recombinant GOOX is performed in a buffer having an ionic strength of at least 100 mM.

6. The process of claim 1, wherein the enzymatic conversion of the 4-O-methyl glucuronic acid to the 4-O-methyl glucaric acid by the recombinant GOOX is performed in the absence of exogenous cofactor supplementation.

7. The process of claim 1, wherein the enzymatic conversion of the 4-O-methyl glucuronic acid to the 4-O-methyl glucaric acid by the recombinant GOOX is performed at a temperature between 38° C. and 42° C.

8. The process of claim 1, further comprising enzymatic treatment of a polysaccharide comprising 4-O-methyl glu-curonic acid moieties with a glycoside hydrolase to release the 4-O-methyl glucuronic acid prior to enzymatic conversion of the 4-O-methyl glucuronic acid to the 4-O-methyl glucaric acid by the recombinant GOOX.

9. The process of claim 8, wherein the enzymatic treatment of the polysaccharide to release the 4-O-methyl glucuronic acid and the enzymatic conversion of the 4-O-methyl glucuronic acid to the 4-O-methyl glucaric acid by the recombinant GOOX are performed in the same reaction vessel.

10. The process of claim 8, further comprising the use of a catalase to catalyze the breakdown of hydrogen peroxide generated by the recombinant GOOX.

11. A composition comprising a recombinant gluco-oli-gosaccharide oxidase (GOOX) having at least 99% sequence identity to SEQ ID NO: 1, O-methyl glucuronic acid as a GOOX substrate, and an alkaline reaction buffer enabling enzymatic conversion of the 4-O-methyl glucuronic acid to 4-O-methyl glucaric acid.

12. The composition of claim 11, wherein the recombinant GOOX is immobilized to a solid support, particle, or matrix.

13. The composition of claim 11, wherein the alkaline reaction buffer has a pH of 7.5 to 11.

14. The composition of claim 11, wherein the alkaline reaction buffer has an ionic strength of at least 100 mM.

15. The composition of claim 11, wherein the composition is free of exogenous cofactors.

16. The composition of claim 11, further comprising a catalase to catalyze the breakdown of hydrogen peroxide generated by the recombinant GOOX.

17. The composition of claim 11, wherein the recombinant GOOX comprises 300A, 314A, or 388S, relative to the amino acid positioning of SEQ ID NO: 1.

* * * * *